US008222004B2

(12) United States Patent
Higashida

(10) Patent No.: US 8,222,004 B2
(45) Date of Patent: Jul. 17, 2012

(54) DIAGNOSIS AND TREATMENT OF AUTISM USING CD38

(75) Inventor: Haruhiro Higashida, Ishikawa (JP)

(73) Assignees: National University Corporation Kanazawa University, Ishikawa (JP); Tohoku University, Miyagi (JP)

( * ) Notice: Subject to any disclaimer, the term of this patent is extended or adjusted under 35 U.S.C. 154(b) by 310 days.

(21) Appl. No.: 12/312,505

(22) PCT Filed: Nov. 15, 2007

(86) PCT No.: PCT/JP2007/072603
§ 371 (c)(1),
(2), (4) Date: May 14, 2009

(87) PCT Pub. No.: WO2008/059991
PCT Pub. Date: May 22, 2008

(65) Prior Publication Data
US 2011/0030070 A1      Feb. 3, 2011

(30) Foreign Application Priority Data

Nov. 15, 2006  (JP) ................................ 2006-308920
Dec. 15, 2006  (JP) ................................ 2006-339054

(51) Int. Cl.
*C12P 19/34*       (2006.01)
(52) U.S. Cl. ...................................... 435/91.2; 435/91.1
(58) Field of Classification Search ........................ None
See application file for complete search history.

(56) References Cited

U.S. PATENT DOCUMENTS 7,604,948 B2 * 10/2009 Amaral et al. ................. 435/7.1

FOREIGN PATENT DOCUMENTS

WO    WO 2004/030524 A2    4/2004
WO    WO 2005/115478 A2   12/2005

OTHER PUBLICATIONS

Wassink et al. Am J Med Genet 2001;105:406-13.*
Moreadith et al., J. Mol. Med. 1997;75(3):208-16.*
Mullins, J Clin Invest, 1996;97:1557-60.*
Wall, J Dairy Sci 1997;80:2213-24.*
Denning, Nat Biotech 2001;19:559-562.*
Yanagimachi, Mol Cell Endocrinol 2002;187:241-8.*
Wilmut, Cloning Stem Cell 2003;5:99-100.*
Polejaeva et al, Nature 2000;407:86.*
Levanon, EMBO Reports 2003;4:560-4.*
Iqbal et al. Am J Physiol Renal Physiol 2006;291:F557-66.*
Green et al., "Oxytocin and Autistic Disorder: Alterations in Peptide Forms", Biological Psychiatry, vol. 50, No. 8, Oct. 15, 2001, pp. 609-613, XP002581734.
Supplementary European Search Report for Application No. EP07832332, dated Jun. 2, 2010.
Thompson et al., "Role of CD38 in Myometrial Ca2+ Transients: Modulation by Progesterone", American Journal of Physiology, American Journal of Endocrinology and Metabolism, vol. 287, No. 6, Dec. 2004, pp. E1142-E1148, XP002581733.
Yagui et al., "A Missense Mutation in the CD38 Gene, a Novel Factor for Insulin Secretion: Association with Type II Diabetes Mellitus in Japanese Subjects and Evidence of Abnormal Function when Expressed in Vitro", Diabetologia, vol. 41, No. 9, Sep. 1998, pp. 1024-1028, XP002581735.
Kosfeld, Michael et al., "Oxytocin increases trust in humans" Nature, Jun. 2, 2005, vol. 435, No. 7042, pp. 673-676.
Keverne, Eric B et al., "Vasopressin, oxytocin and social behaviour" Current Opinion in Neurobiology, 2004, vol. 14, No. 6, pp. 777-783.
Kato, Ichiro et al., "CD38 Disruption Impairs Glucose-induced Increases in Cyclic ADP-ribose, [$Ca^{2+}$]$_i$, and Insulin Increases Secretion" The Journal of Biological Chemistry, Jan. 22, 1999, vol. 274, No. 4. pp. 1869-1872.
Young, Genevieve S. et al., "Decreased cADPR and increased $NAD^+$ in the $Cd384^{-/-}$ mouse", Biochemical and Biophysical Research Communications, Jul. 2006, vol. 346, No. 1, pp. 188-192.
Ceni, Claire et al., "The CD38-independent ADP-ribosyl cyclase from mouse brain synaptosomes: a comparative study of neonate and adult brain", The Biochemical Journal Apr. 2006, vol. 395, No. 2, pp. 417-426.
Jin, Duo et al., CD38 is critical for social behaviour by regulating oxytocin secretion, Nature, Mar. 1, 2007, vol. 446, No. 7131, pp. 41-45.

* cited by examiner

*Primary Examiner* — Q. Janice Li
(74) *Attorney, Agent, or Firm* — Birch, Stewart, Kolasch & Birch, LLP

(57) ABSTRACT

The invention relates to a method for screening a pharmaceutical for treating or preventing a neurodevelopmental disorder or a psychiatric disorder accompanied by an abnormality of oxytocin system by using an increase in expression or enzymatic activity of CD38 as an index, and a diagnosis of a predisposition to a neurodevelopmental disorder or a psychiatric disorder accompanied by an abnormality of oxytocin system by using a mutation present in a CD38 gene region as an index.

4 Claims, 15 Drawing Sheets
(6 of 15 Drawing Sheet(s) Filed in Color)

DIAGNOSIS AND TREATMENT OF AUTISM USING CD38

TECHNICAL FIELD

The present invention relates to use of CD38 in diagnosis and treatment of neurodevelopmental disorders or psychiatric disorders accompanied by an abnormality in oxytocin system, represented by autism.

BACKGROUND ART

Autism is a developmental disorder that exhibits retardation in development of sociality and communication skills. In Japan, it is said that an incidence of autism is 1 to 2 in every 1000 people, though this figure may vary depending on how to define a scope of autism. According to announcements from Autism Society Japan, it is estimated that 360,000 people across Japan are affected by autism, and that 1.2 million people have autism when including high functioning autism (Asperger disorder) and the like, which are not accompanied by mental retardation or speech disturbance.

Various causes such as lack of affection, brain disorders, and environmental factors (mercury accumulation) have been proposed as to development of autism. Currently, the most widely accepted theory is that a genetic predisposition is responsible for autism, and many genetic factors are considered to participate therein. For information, schizophrenia, which is supposedly regarded as a genetic disease, affects both monozygotic twins with an incidence of 50%. By contrast, autism affects both monozygotic twins with an incidence of 90%, and familial clustering thereof is also observed.

For example, it has been reported that a HOXA1 gene is highly probably associated with development of autism (Ingram et al., Teratology. 2000 December; 62 (6): 393-405). HOXA1, which is a transcription factor-encoding gene located on chromosome 7, has been found to be important for neuronal differentiation and development. Autistic individuals have a high probability of mutations seen in repeat polymorphism sites in this gene. In addition, it has also been reported that genes associated with autism with developmental regression are located on chromosome 7 and chromosome 21 (Molloy et al., Mol Psychiatry. 2005 August; 10 (8): 741-746).

Recently, attention has been paid to association of pituitary hormone oxytocin with psychiatric disorders. Oxytocin, which is a 9-amino-acid long peptide hormone, has been known to have effects of promoting lactation and promoting uterine contraction, and its receptors are also present in central nervous system and present even in males. For example, it has been reported that some autistic individuals have lower plasma oxytocin levels (Modahl et. al. Biol. Psychiatry. 1998 February; 43 (4): 270-277) and that oxytocin receptor-knockout mice exhibit social behavior abnormalities (Takayanagi et al., Proc Natl Acad Sci USA. 2005 Nov. 1; 102 (44): pp 16096-16101). Fehr et al. have reported that when 194 students received intranasal administration of oxytocin or placebo and then played an "investment game", the group receiving oxytocin invested more money and more frequently invested a maximum allowable than the placebo group (Kosfeld et al., Nature. 2005 Jun. 2; 435 (7042): pp 673-676). This result indicates that administration of oxytocin increases trust in others and individual's willingness to accept risks, that is, oxytocin promotes prosocial behaviors.

CD38, a 45-kDa single-transmembrane protein, is an ectoenzyme whose catalytic activity (NAD degrading activity) is located on an extracellular domain. CD38 has been known to be expressed on activated T and B cells, NK cells, monocytes, plasma cells, and medullary thymocytes, and this expression has been considered to depend on differentiation and activation of the cells. CD38 is widely used as a marker in studies of T and B cell activation and also clinically utilized in diagnosis of hematologic malignancies and in diagnosis of autoimmune diseases, AIDS, and aplastic anemia. Other various reports have been made on the activity and nature of CD38, particularly in the field of control of immune responses. However, no document has reported its association with psychiatric disorders or oxytocin release.

SUMMARY OF THE INVENTION

Problems to be Solved by the Invention

Psychiatric disorders including autism are multifactorial diseases that develop due to a complicated mixture of environmental and genetic predispositions, and diagnosis and treatment thereof are not easy. Moreover, there are plural types of autism differing in causes or characteristics, and identification of each type and selection of treatment effective therefor are not easy.

Means for Solving the Problems

The present inventor prepared CD38-knockout (−/−) mice for examining functions of CD38 and examined their phenotypic differences from wild-type mice. As a result, the present inventor found that the knockout mice exhibit a behavior abnormality (hyperactivity) characteristic in autistic individuals and a remarkable decrease in plasma oxytocin level. Thus, oxytocin was supplemented to the mice by subcutaneous injection of oxytocin or introduction of a human CD38 gene. As a result, it was confirmed that the mice recover from the behavior abnormality. Furthermore, the present inventor and colleagues examined a relationship between CD38 deficiency and a decrease in oxytocin level and revealed a mechanism underlying control of oxytocin release by CD38. No previous report has been made on the relationship between CD38 and oxytocin release or psychiatric disorders such as autism. These findings indicated a possibility of novel approaches for treatment or prevention of such psychiatric disorders.

Specifically, the present invention provides a method of evaluating a pharmaceutical agent for treating or preventing a neurodevelopmental disorder or psychiatric disorder accompanied by an abnormality in oxytocin system, characterized in that a therapeutic or preventive effect of a test substance on the neurodevelopmental disorder or psychiatric disorder is evaluated based on an increase in expression or enzymatic activity of CD38 due to administration of the test substance. In this context, examples of the neurodevelopmental disorder or psychiatric disorder accompanied by an abnormality in oxytocin system include autism, Asperger syndrome, hyperactivity disorder, learning/memory impairment and the like.

In the method, the increase in expression or enzymatic activity of CD38 can be evaluated based on, for example, a CD38 expression level as well as an activity of a cADPR- and/or NAADP-producing enzyme, a cADPR- and/or NAADP-dependent intracellular calcium concentration, or a CD38-dependent oxytocin release activity.

As to the evaluation method performed in vitro, for example, isolated hypothalamic neurons or pituitary nerve terminals are treated with the test substance and the test substance can be determined to be useful as a pharmaceutical agent for treating or preventing a neurodevelopmental disorder or psychiatric disorder accompanied by an abnormality in oxytocin system when the test substance significantly increases a CD38 expression level, an activity of a cADPR- and/or NAADP-producing enzyme, a cADPR- and/or NAADP-dependent intracellular calcium concentration, or a CD38-dependent oxytocin release activity in the cells compared to that before the treatment.

Examples of the evaluation method performed in vivo can include a method using a transgenic non-human mammal deficient in CD38 function in both alleles on a chromosome. Specifically, the test substance is administered to the transgenic non-human mammal deficient in CD38 function in both alleles on a chromosome and the test substance can be determined to be useful as a pharmaceutical agent for treating or preventing a neurodevelopmental disorder or psychiatric disorder accompanied by an abnormality in oxytocin system when the animal exhibits an increase in plasma oxytocin level and/or recovery from behavior abnormalities.

The present invention also provides use of a transgenic non-human mammal deficient in CD38 function in both alleles on a chromosome as a model animal of a neurodevelopmental disorder or psychiatric disorder accompanied by an abnormality in oxytocin system.

The present invention also provides a method of determining a predisposition of a subject to a neurodevelopmental disorder or psychiatric disorder accompanied by an abnormality in oxytocin system by detecting a mutation in a CD38 gene region in a sample isolated from the subject.

Examples of the mutation in a CD38 gene region include mutations that lead to a substitution of tryptophan for arginine at position 140 in CD38 amino acid sequence of SEQ ID NO: 2, for example, a substitution of thymine for cytosine at position 4693 in CD38 gene of SEQ ID NO: 1.

Advantages of the Invention

The present invention allows diagnosis (particularly, diagnosis on a type-by-type basis) of a predisposition to or treatment of psychiatric disorders associated with an abnormality in oxytocin system, such as autism, which were previously difficult to diagnose or treat.

The patent or application file contains at least one drawing executed in color. Copies of this patent or patent application publication with color drawing(s) will be provided by the office upon request and payment of the necessary fee.

BRIEF DESCRIPTION OF THE DRAWINGS

FIG. 12a: olfactory investigation time after introduction of a CD38 gene (+Lenti-CD38: WT), a mutated CD38 gene (+Lenti-CD38: R140W), or GFP (+Lenti-GFP) into CD38-knockout mice, FIG. 12b: 4th olfactory investigation time relative to 1st time (%); after introduction of a CD38 gene (WT, second right column), a mutated CD38 gene (R140W, rightmost column), or GFP (+GFP, third right column).

Figure 1:
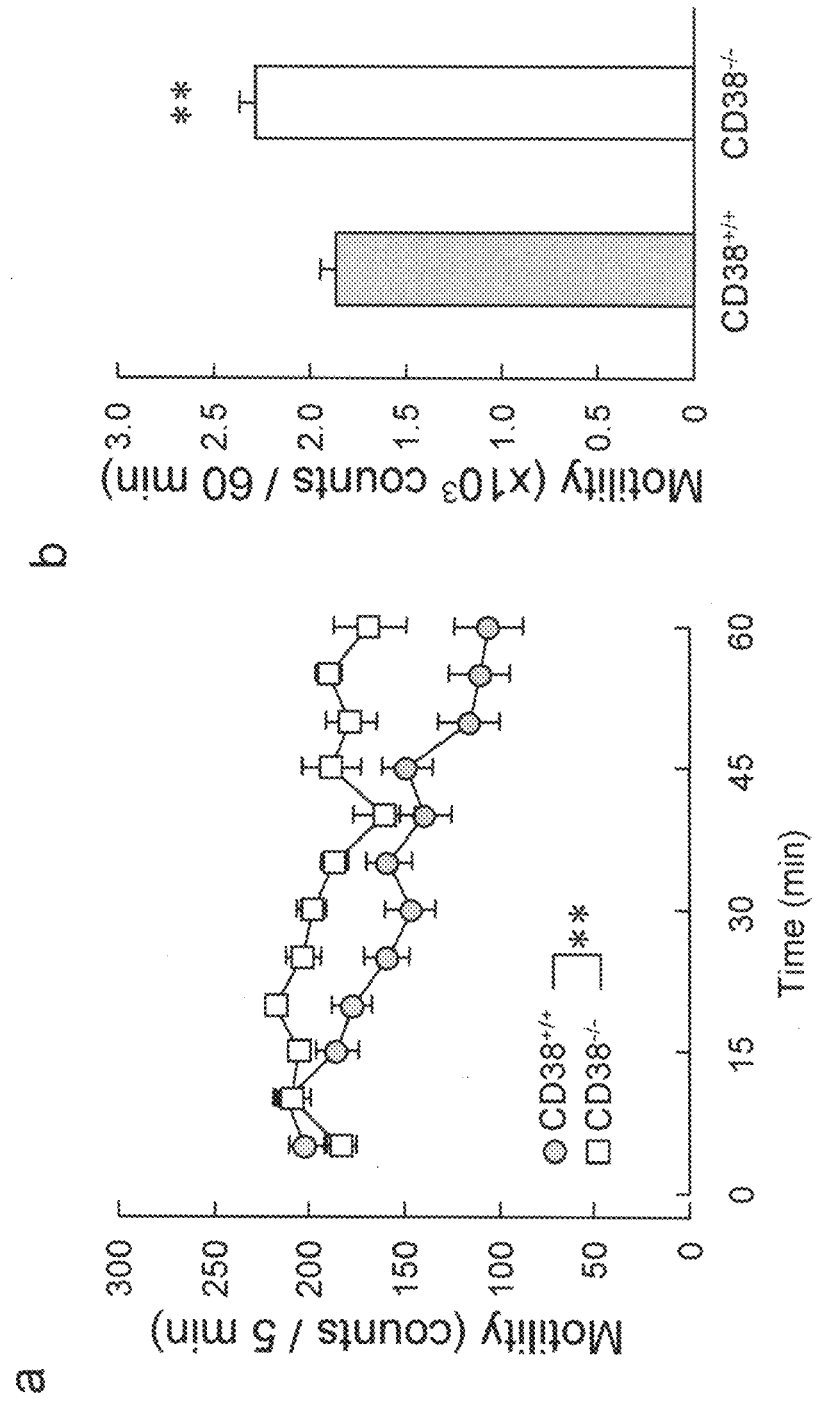
FIG. 1 shows spontaneous motilities of wild-type (N=11) and CD38−/− (N=8) mice (FIG. 1a: changes over time, FIG. 1b: mean per mouse (60 min.)).

The present specification encompasses contents described in specifications of Japanese Patent Application Nos. 2006-308920 and 2006-339054 which serve as a basis for the priority of the present application.

BEST MODE FOR CARRYING OUT THE INVENTION

1. Oxytocin and Psychiatric Disorder

Oxytocin is a 9-amino-acid long peptide hormone released from posterior pituitary. Well known effects of oxytocin are those of promoting lactation and promoting uterine contrac-

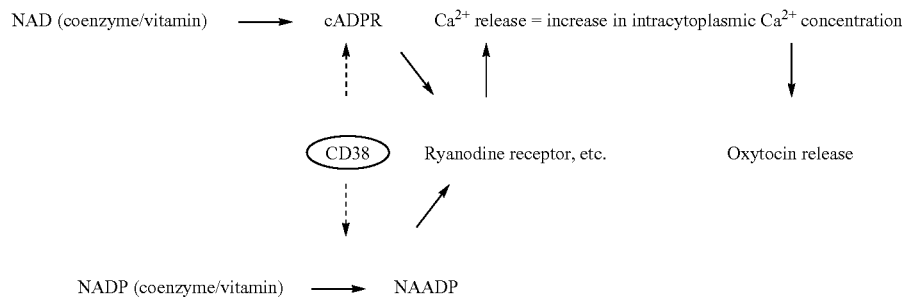

tion. In addition, its insulin-like effects in lipid metabolism have been reported. Recently, an association of oxytocin or oxytocin receptors with psychiatric disorders including autism has been reported, and application of oxytocin to patients with psychiatric disorders has been expected. Particularly, oxytocin has effects of promoting prosocial behaviors and trust in others and has therefore been considered to be useful for symptoms such as social phobia, individuals having difficulty in social life or group behaviors, and autism, Asperger syndrome, hyperactivity disorder, and learning/memory impairment with problems in social behaviors or group behaviors. In the present invention, the term "a neurodevelopmental disorder or psychiatric disorder accompanied by an abnormality in oxytocin system" refers to a neurodevelopmental disorder or psychiatric disorder that exhibits and may be caused by deficiency, decreased expression level, decreased release, decreased activity, or localization of oxytocin or by a state similar to failure of oxytocin release due to, for example, deficiency, decreased expression level, decreased function, or localization of oxytocin receptors. Examples thereof include autism, Asperger syndrome, hyperactivity disorder, and learning/memory impairment.

2. CD38 and Oxytocin Release

CD38, a 45-kDa single-transmembrane protein, is an ectoenzyme whose catalytic activity (NAD degrading activity) is located on an extracellular domain. CD38 antigen is mainly expressed on most hematopoietic cells in a duration of early differentiation and activation. CD38 is expressed on B and T cell precursors in bone marrow and thymus, and down-regulated in resting cells, while it is re-expressed upon cell activation, with very high expression observed on terminally differentiated B cells (plasma cells). Therefore, CD38 is widely used as a marker in studies of T and B cell activations and also utilized in diagnosis of hematologic malignancies and in diagnosis of autoimmune diseases, AIDS, and aplastic anemia.

The present inventor and colleagues found and demonstrated for the first time that CD38-knockout (−/−) mice exhibit behavior abnormalities similar to autism, and those behavior abnormalities are due to decreased oxytocin release caused by deficiency in CD38 function.

Furthermore, the present inventor and colleagues revealed processes of control of oxytocin release by CD38, from results of in vivo or in vitro experiments using CD38-knockout (−/−) mice. These processes are summarized below:

Oxytocin release from hypothalamic or pituitary neurons is considered as controlled by an increase in intracellular $Ca^{2+}$ concentration mediated by ryanodine receptors using cyclic ADP-ribose (cADPR) or nicotinate adenine dinucleotide phosphate (NAADP) as a second messenger. Of the pathways, CD38 acts on cADPR or NAADP production from NAD or NADP such that cADPR or NAADP levels are increased to promote oxytocin release.

3. Screening for a Pharmaceutical Agent for Treating or Preventing a Psychiatric Disorder Accompanied by Abnormality in Oxytocin Using CD38

1) In Vitro Screening

In in vitro screening using isolated cells, expression level or enzymatic activity of CD38 can be evaluated using a CD38 gene expression level, an activity of a cADPR- and/or NAADP-producing enzyme, a cADPR- and/or NAADP-dependent intracellular calcium concentration, or a CD38-dependent oxytocin release activity as an index. In the present invention, the term "a cADPR- and/or NAADP-dependent intracellular calcium concentration" means an amount of intracellular Ca increased by a stimulation to isolated nerve terminals with a solution containing 50 mM potassium ions, which is suppressed by a cADPR or NAADP inhibitor. The term "a cADPR- and/or NAADP-dependent oxytocin release activity" means an amount of oxytocin released from nerve terminals or the like due to cADPR or NAADP supplied extracellularly.

Cells used are preferably hypothalamic neurons or pituitary nerve terminals. For example, hypothalamic neurons or pituitary nerve terminals are treated with a test substance, and cADPR and/or NAADP levels in the cells are measured and compared with that before the test substance treatment. The test substance can be determined to be useful as a pharmaceutical agent for treating or preventing a neurodevelopmental disorder or psychiatric disorder accompanied by an abnormality in oxytocin system when a measured cADPR and/or NAADP level is significantly (e.g., $p<0.05$) increased compared to that before the treatment. Likewise, the test substance can be determined to be useful as a pharmaceutical agent for treating or preventing a neurodevelopmental disorder or psychiatric disorder accompanied by an abnormality in oxytocin system when a cADPR- and/or NAADP-dependent intracellular calcium concentration is significantly (e.g., p<0.05) increased compared to that before the treatment. Alternatively, the test substance can be determined to be useful as a pharmaceutical agent for treating or preventing a neurodevelopmental disorder or psychiatric disorder accompanied by an abnormality in oxytocin system when a cADPR- and/or NAADP-dependent oxytocin concentration, that is, a release activity, during culture is significantly (e.g., p<0.05) increased compared to that before the treatment.

Moreover, similar evaluation can be conducted using hypothalamic neurons or pituitary nerve terminals isolated from a CD38-deficient non-human mammal (mouse) described in next paragraph. In this case, the evaluation may also be conducted using a degree of its response (sensitivity) as an index.

A cADPR and/or NAADP level can be determined by immunoassay using antibodies specific to the protein or a part thereof, affinity chromatography, or two-dimensional electrophoresis. Specific examples of the immunoassay include western blot, enzyme immunoassay (EIA), enzyme-linked immunosorbent assay (ELISA), microparticle enzyme immunoassay (MEIA), fluorescence enzyme immunoassay (FEIA), fluorescence polarization immunoassay (FPIA), chemiluminescence immunoassay (CLIA), sandwich binding protein assay (SBPA), and radioimmunoassay (RIA). For detailed information about these immunoassays, ordinary molecular biological and biochemical textbooks can be referred to, such as Sambrook et al., ed., Molecular Cloning, A Laboratory Manual, 3rd ed., (2001) (Cold Spring Harbor Laboratory Press, New York) and Ausubel et al., ed., Current Protocols in Molecular Biology (Wiley. Interscience, New York). In this context, the term "level" is not limited to an amount of a protein and also encompasses a titer (antibody titer, etc.) that indirectly indicates an amount thereof.

Antibodies used for detection can be prepared according to a method known in the art or may be commercially available. For example, animals are immunized with an antigen, and antibodies produced in the animals can be collected and purified to obtain the antibodies of interest. Alternatively, according to a method known in the art (e.g., Kohler and Milstein, Nature 256, 495-497, 1975; and Kennet, R. ed., Monoclonal Antibody p. 365-367, 1980, Plenum Press, N.Y.), antibody-producing cells that produce specific antibodies are fused with myeloma cells to thereby establish hybridomas, from which a monoclonal antibody can in turn be obtained.

Examples of antigens for antibody preparation can include an antigen protein, a polypeptide having a partial sequence comprising at least 6 consecutive amino acids thereof (polypeptide of an epitope region), and derivatives thereof comprising an arbitrary amino acid sequence or carrier (e.g., keyhole limpet hemocyanin added N-terminally) added to such sequence. Antigen polypeptides can be obtained by production from host cells through genetic engineering.

Antibodies are labeled directly or used as primary antibodies in conjunction with labeled secondary antibodies that specifically recognize the primary antibodies (recognize antibodies derived from an animal used in antibody preparation) for detection. The type of the label is preferably, but not limited to, an enzyme (alkaline phosphatase or horseradish peroxidase) or biotin (which, however, needs further procedures of binding of enzyme-labeled streptavidin to the biotin labels on the secondary antibodies). Various antibodies (or streptavidin) labeled in advance are commercially available as labeled secondary antibodies (or labeled streptavidin). In RIA, antibodies labeled with a radioisotope such as $^{125}I$ are used, and measurement is performed using a liquid scintillation counter or the like. An activity of these enzyme labels is detected to thereby determine an expression level of the antigen. When alkaline phosphatase or horseradish peroxidase is used for labeling, substrates are commercially available, which develop color or emit light by catalytic activity of these enzymes.

When substrates which develop color are used, the color can be detected by visual observation using western blot or dot/slot blot. For ELISA, it is preferred that an absorbance (a wavelength for measurement may vary depending on substrates) of each well is measured using a commercially available microplate reader to quantify the antigen. Alternatively, dilution series of an antigen used in antibody preparation are prepared, and these dilution series are used as standard antigen samples which are detected simultaneously with other samples to prepare a standard curve that shows measured values plotted against standard antigen concentrations. Based on this standard curve, antigen concentrations in the other samples can be quantified. When the substrates which emit light are used in western blot or dot/slot blot, the light can be detected by autoradiography using an X-ray film or an imaging plate or by photography using an instant camera. Moreover, quantification may also be performed using densitometry, Molecular Imager Fx System (manufactured by Bio-Rad Laboratories, Inc.), or the like. Furthermore, when substrates which emit light are used in ELISA, an enzymatic activity is measured using a luminescence microplate reader (manufactured by e.g., Bio-Rad Laboratories, Inc.).

2) In Vivo Screening (use of CD38-Deficient Non-Human Mammal)

In vivo screening may be performed using a CD38-deficient non-human mammal (transgenic non-human mammal deficient in CD38 function in both alleles on a chromosome) described later. In this case, a test substance is administered to the CD38-deficient non-human mammal, and the test substance can be determined to be useful as a pharmaceutical agent for treating or preventing a psychiatric disorder accompanied by an abnormality in oxytocin system when the animal exhibits an increase in plasma oxytocin level and/or recovery from behavior abnormalities. A method of preparing a CD38-deficient non-human mammal is described in detail in next section.

In this context, oxytocin level can be measured by immunoassay using antibodies specific to oxytocin or a part thereof, affinity chromatography, or two-dimensional electrophoresis. Details thereof are as described above.

4. CD38-Deficient Non-Human Mammal 4.1 Definition

A CD38-deficient non-human mammal used in the present invention refers to "a transgenic non-human mammal deficient in CD38 function in both alleles on a chromosome".

Nucleotide sequences of "CD38 gene" are known in the art as to mammals such as mice, rats, and humans and can readily be obtained through public databases such as GenBank (e.g., mouse: GenBank Accession No. AB016868, human: GenBank Accession No. D84284). Alternatively, for an animal whose CD38 nucleotide sequence is not registered in public databases, its CD38 gene can be cloned based on homology to known CD38 genes according to a standard method and can be sequenced. Specifically, a genomic DNA library of an animal is prepared and screened using, as a probe, a known CD38 gene or a part thereof from a species genetically closest thereto to identify a CD38 gene of interest, which may then be sequenced.

The phrase "deficient in CD38 function in both alleles on a chromosome" means that a CD38 gene on a chromosome is disrupted in both alleles such that its function is not normally exhibited. Specifically, the phrase "deficient in CD38 function in both alleles on a chromosome" encompasses not only a case where no CD38 gene product is expressed but also a case where gene products, even if expressed, do not normally function as CD38. Such disruption of CD38 gene can be caused by modifications such as deletion or substitution of a partial sequence, and/or insertion of other sequence in CD38 gene or in its expression regulatory region including a transcriptional regulatory region and a promoter region. In this context, a site where the deletion, substitution, or insertion occurs, or the deleted, substituted, or inserted sequence is not particularly limited as long as it causes deficiency of normal functions of CD38 gene. However, a mutation that deletes a majority (e.g., 50% or more, preferably 80% or more, particularly preferably 90% or more) of a coding region of CD38 gene can reliably abolish CD38 gene functions. An approach of causing such deficiency of CD38 gene functions is described in detail in next section.

"A non-human mammal" is not particularly limited as long as it is a mammal other than a human. A non-human mammal is preferably a rodent such as a mouse, rat, or rabbit, particularly preferably a mouse which can readily be genetically engineered using an established ES cell technique.

4.2 Method of Preparing CD38-Deficient Animal

A CD38-deficient animal used in the present invention can be prepared by using a technique such as gene targeting, a Cre-loxP system, or somatic cell clones.

(1) Gene Targeting

Gene targeting is an approach by which a particular gene on a chromosome is mutated through use of homologous recombination (Capecchi, M. R. Science, 244, 1288-1292, 1989; and Thomas, K. R. & Capecchi, M. R. Cell, 44, 419-428, 1986).

1) Construction of Targeting Vector

First, a targeting vector is constructed for causing deficiency of CD38 gene. Prior to construction of the targeting vector, a genomic DNA library of an animal used is prepared. A library prepared from genomic DNAs isolated from ES cells of the animal used or genomic DNAs of a strain from which the cells are derived must be used as this genomic DNA library to prevent a recombination frequency from being reduced due to polymorphisms or the like. Such a library may be commercially available (e.g., 129Sv/J Genomic Library, manufactured by Stratagene). The genomic library is screened using CD38 cDNA of interest or a partial sequence thereof as a probe, to clone CD38 genomic DNA.

The cloned genomic DNA is subjected to sequencing, southern blotting, restriction enzyme digestion, and so on to thereby prepare a restriction enzyme map that shows a position of each exon. Based on the map, a mutagenesis site, etc. are determined. Moreover, probes for screening of homologous recombinants (external probes) are set externally to the homologous regions used in the targeting vector.

In the present invention, a mutation (deletion, substitution, or insertion) introduced on a chromosome is not particularly limited as long as it causes deficiency of normal functions of CD38 gene. For example, a deleted or substituted sequence may be in an intron or exon region in CD38 gene or may be in an expression regulatory region in CD38 gene. Particularly, a mutation that deletes a majority (e.g., 50% or more, preferably 80% or more, particularly preferably 90% or more) of a coding region of CD38 gene can reliably abolish CD38 gene functions. Moreover, other sequences inserted therein are not particularly limited and may be, for example, various marker gene sequences as described below.

A targeting vector contains homologous regions 3' and 5' to the mutagenesis site and, an appropriate selective marker for selecting recombinants. Examples of the marker include, but not limited to, positive selection markers such as neomycin resistance genes (pGKneo, pMC1neo, etc.), β-lactamase genes, and hygromycin B phosphotransferase genes, and negative selection markers such as herpes simplex virus thymidine kinase (HSV-TK) genes and diphtheria toxin A (DT-A) fragments. Moreover, the vector contains appropriate restriction sites for linearizing the vector, externally to the homologous regions.

Construction of such targeting vector can be performed preferably using a commercially available plasmid vector (e.g., pBluescript II (manufactured by Stratagene)).

2) Introduction of Targeting Vector into ES Cells

Next, the constructed targeting vector is introduced into cells having totipotency, such as embryonic stem cells (ES cells). ES cells have already been established as cell lines for mice, hamsters, pigs, etc. Particularly, plural cell lines can be obtained for mice, such as K14, E14, D3, AB-1, J1, R1, and TT2 cell lines from mice of 129 strain. Alternatively, embryonic carcinoma cells (EC cells) can be used for mice instead of ES cells.

ES cells are cultured in an appropriate medium prior to introduction of the targeting vector. For example, mouse ES cells are cocultured with feeder cells such as mouse fibroblasts supplemented with a liquid medium for ES cells (manufactured by e.g., GIBCO).

The targeting vector can be introduced into ES cells by a gene transfer technique known in the art, such as electroporation, microinjection, or a calcium phosphate method. ES cells successfully transfected with the targeting vector can be selected easily by use of a marker inserted in the vector. For example, transfected cells that contain a neomycin resistance gene as a marker can be primarily selected by culturing in a medium for ES cells supplemented with G418.

In the ES cells thus transfected with the targeting vector, a part of CD38 gene on a chromosome is substituted by the vector sequence through homologous recombination such that the endogenous CD38 gene is disrupted. Success or failure of the desired homologous recombination can be determined by genotypic analysis using southern blotting, PCR, or the like. The genotypic analysis using southern blotting can be conducted using probes set externally to the mutagenesis site (external probes). The genotypic analysis using PCR can be conducted by detecting amplification products specific for each of wild-type and a mutated CD38 gene. The ES cells thus properly transfected with the targeting vector are further cultured for next step.

3) Preparation of Chimeric Animal

The ES cells transfected with the targeting vector (recombinant ES cells) are introduced into early embryos from another strain evidently different in appearance from the strain from which the ES cells are obtained. These embryos are allowed to develop as chimeric animals. It is preferred for mice that, for example, ES cells from mice of 129 strain having albino's hair color should be introduced into early embryos of C57BL/6 mice which have black hair color and differ in various gene loci available as markers from the mice of 129 strain. As a result, the rate of chimerism can be determined based on the hair color of the chimeric mice.

Introduction of ES cells into early embryos can be performed by a microinjection method (Hogan, B. et al. "Manipulating the Mouse Embryo" Cold Spring Harbor Laboratory Press, 1988), aggregation method (Andras, N. et al. Proc. Natl. Acad. Sci. USA, 90, 8424-8428, 1993; and Stephen, A. W. et al. Proc. Natl. Acad. Sci. USA, 90, 4582-4585, 1993), etc.

The microinjection method is a method by which ES cells are directly injected into blastocysts. Specifically, recombinant ES cells are directly injected under a microscope into blastocysts collected from animals, using a micromanipulator or the like to prepare chimeric embryos. These chimeric embryos can be transplanted into uteri of foster mothers (pseudopregnant animals) and allowed to develop to obtain desired chimeric animals.

In the aggregation method, a mass of ES cells is inserted hold between two embryos at an 8-cell stage after removal of zona pellucida and cultured for aggregation to obtain chimeric embryos. These chimeric embryos can be transplanted into uteri of foster mothers (pseudopregnant animals) and allowed to develop to obtain chimeric animals.

4) Preparation of CD38-Deficient Animal Strain

Chimeric animals obtained from foster mothers are further crossed with wild-type animals of the same strain. Approximately half of obtained newborn animals are supposed to be heterozygous for a chromosome with CD38 gene deletion. A genotype of each individual can be determined primally based on apparent characteristics such as hair color or can also be determined by a genotypic analysis using southern blotting or PCR described above. Heterozygous CD38-deficient animals thus identified can be crossed with each other to obtain animals homozygous for deficiency of CD38 gene.

CD38-deficient animals of the present invention encompass both of animals heterozygous for deficiency of CD38 gene and animals homozygous therefor. CD38-deficient animals of the present invention further encompass offspring of the CD38-deficient animals thus prepared as long as they are deficient in CD38 gene functions on their chromosomes.

(2) Use of Cre-loxP System

Another method of gene targeting utilizes a Cre-loxP system from bacteriophage P1 to cause deficiency of a target gene in site-specific and time-specific manners (Kuhn R. et al., Science, 269, 1427-1429, 1995). The loxP (locus of X-ing-over) sequence, a 34-bp DNA sequence, is recognized by Cre (Causes recombination) recombinase. Two loxP sequences on a gene lead to specific recombination in the presence of Cre protein. Specifically, if a target gene to be deleted is replaced by that flanked by loxP sequences, and a Cre expression vector is incorporated, the loxP-flanked target gene may be deleted through site-specific/time-specific Cre protein production.

For example, a targeting vector comprising a CD38 gene region to be deleted which is 5' flanked by a loxP gene and 3' flanked by a loxP-flanked marker gene (neomycin resistance gene, etc.) is prepared according to the preceding paragraph 1) and introduced into ES cells. The ES cells are selected by use of the marker and then subjected to genotypic analysis using southern blotting or PCR to confirm successful homologous recombination. These homologously recombinant ES cells are further transfected with a Cre expression vector comprising a Cre protein-encoding gene ligated with a specific promoter. From the resulted ES cells, ES cell clones are identified which have deletion only of the marker gene through loxP recombination without deletion of the CD38 gene region. These ES cells are introduced into animals according to the preceding paragraphs 3) and 4) to obtain Cre-loxP recombinant animals.

Alternatively, loxP-containing recombinant animals in which a targeting vector comprising a CD38 gene flanked by loxP genes on both ends has been introduced and Cre-expressing recombinant animals in which a Cre expression vector has been introduced may be prepared separately and crossed with each other to obtain Cre-loxP recombinant animals.

The resulted Cre-loxP recombinant animals can be deficient in CD38 gene in site-specific and time-specific manners according to Cre protein expression. Thus, they are exceedingly useful for functional analysis of CD38 gene at a particular time and a particular site.

(3) Somatic Cell Clones

For animals having no available ES cells, CD38-deficient animals may be prepared using somatic cell clones (I. Wilmut et al, Nature, Vol. 385, 810-813, 1997; and A. E. Schnieke et al, Science, Vol. 278, 2130-2133, 1997). Somatic cell clones are clones which are prepared by transplanting nuclei isolated from somatic cells to enucleated unfertilized eggs to prepare clone embryos, which are in turn transplanted into uteri of foster mothers and allowed to develop. These somatic cell clones can be combined with a gene transfer technique to obtain desired recombinant animal clones. Specifically, nuclei are isolated from somatic cells that have undergone in advance recombination procedures for causing deficiency of CD38 gene, and these nuclei are transplanted to enucleated unfertilized eggs to prepare clone embryos, which are in turn transplanted into uteri of foster mothers (pseudopregnant animals) to obtain somatic cell clone animals. The resulted animals are deficient in CD38 gene.

4.3 Application of CD38-Deficient Non-Human Mammal

As described above, transgenic non-human mammals deficient in CD38 functions in both alleles on a chromosome has a much lower plasma oxytocin level than that of a wild-type animal and exhibits behavior abnormalities which are seen in a neurodevelopmental disorder or psychiatric disorder accompanied by an abnormality in oxytocin system, such as autism. Hence, a CD38-deficient non-human mammal is useful as a model animal of such neurodevelopmental disorder or psychiatric disorder in studies of pathology thereof or development of therapeutic drugs (screening system) therefor.

5. Diagnosis of Neurodevelopmental Disorders or Psychiatric Disorders Accompanied by an Abnormality in Oxytocin System Based on a Mutation in CD38 Gene The present inventor and colleagues examined chromosomes of autistic individuals and found that a single-nucleotide polymorphism from C to T (substitution of thymine for cytosine at nucleotide No. 4693 in SEQ ID NO: 1) is observed with high frequency in exon 3 region of CD38 gene. This mutation is a newly revealed polymorphism leading to a substitution of tryptophan for arginine at position 140 in a CD38 amino acid sequence of SEQ ID NO: 2. This mutation highly probably leads to reduced sociality via failure of oxytocin release. Accordingly, deletion of this mutation in CD38 gene region enables us to examine a genetic predisposition to, for example, autism, Asperger syndrome, hyperactivity disorder, or learning/memory impairment accompanied by an abnormality in oxytocin system. The mutation can be analyzed by any method known in the art, which can be utilized by those skilled in the art for detecting SNPs or sequence mutations using genomic DNA or mRNA extracted/purified according to a standard method from a biological sample or using cDNA obtained therefrom (see e.g., Orita et al., Proc. Natl. Acad. Sci., 86: 2766-2770). Examples of specific approaches available for such analyses include, but not limited to, CAPS (Cleaved Amplified Polymorphic Sequence), PCR-direct sequencing [Biotechniques, 11, 246-249 (1991)], AP-PCR (Arbitrarily Primed-PCR) [Nucl. Acids Res., 18, 7213-7218 (1990)], PCR-SSCP (single strand conformation polymorphism) [Biotechniques, 16, 296-297 (1994); and Biotechniques, 21, 510-514 (1996)], ASO (Allele Specific Oligonucleotide) hybridization [Clin. Chim. Acta, 189, 153-157 (1990)], ARMS (Amplification Refracting Mutation System) [Nucl. Acids. Res., 19, 3561-3567 (1991); and Nucl. Acids. Res., 20, 4831-4837 (1992)], DGGE (Denaturing Gradient Gel Electrophoresis) [Biotechniques, 27, 1016-1018 (1999)], RNase A cleavage [DNA Cell. Biol., 14, 87-94 (1995)], chemical cleavage [Biotechniques, 21, 216-218 (1996)], DOL (Dye-labeled Oligonucleotide Ligation) [Genome Res., 8, 549-556 (1998)], MALDI-TOF/MS (Matrix Assisted Laser Desorption-time of Flight/Mass Spectrometry) [Genome Res., 7, 378-388 (1997); and Eur. J. Clin. Chem. Clin. Biochem., 35, 545-548 (1997)], TDI (Template-directed Dye-terminator Incorporation) [Proc. Natl. Acad. Sci. USA, 94, 10756-10761 (1997)], Padlock Probe [Nat. Genet., 3, p 225-232 (1998); Genetic Medicine (Idenshi Igaku in Japanese), 4, p 50-51 (2000)], Molecular Beacons [Nat. Biotechnol., 1, p 49-53 (1998); and Genetic Medicine (Idenshi Igaku in Japanese), 4, p 46-48 (2000)], TaqMan PCR [Genet. Anal., 14, 143-149 (1999); and J. Clin. Microbiol., 34, 2933-2936 (1996)], Invader method [Science, 5109, 778-783 (1993); J. Biol. Chem., 30, 21387-21394 (1999); and Nat. Biotechnol., 17, 292-296 (1999)], DASH (Dynamic Allele-Specific Hybridization) [Nat. Biotechnol., 1, p 87-88, (1999); and Genetic Medicine (Idenshi Igaku In Japanese), 4, p 47-48 (2000)], UCAN [see Takara Shuzo Co., Ltd. homepage (http://www.takara.co.jp)], and a method using a DNA chip or DNA microarray [Genomics 4, (1989), Drmanac, R., Labat, I., Brukner, I. and Crkvenjakov, R., p 114-128; and Bio Industry Vol. 17 No. 4, "DNA Chip Technique" p 5-11 (2000)]. Prior to detection, exon 3 region of CD38 gene is appropriately amplified by PCR or RT-PCR. When substitution of thymine for cytosine at nucleotide No. 4693 in CD38 gene of SEQ ID NO: 1 is found in a sample from a subject, the subject can be determined to be an individual having a genetic predisposition to a neurodevelopmental disorder or psychiatric disorder accompanied by an abnormality in oxytocin system (e.g., autism, Asperger syndrome, hyperactivity disorder, or learning/memory impairment).

6. Kit

Anti-cADPR and/or anti-NAADP antibodies can be used as a kit for evaluating a pharmaceutical agent for treating or preventing a neurodevelopmental disorder or psychiatric disorder accompanied by an abnormality in oxytocin system according to the present invention.

Anti-cADPR and/or anti-NAADP antibodies can be prepared according to the method described above. The antibodies may be labeled with an appropriate label (e.g., enzymatically, radioactively, or fluorescently labeled) or may be modified appropriately with biotin or the like. Moreover, the antibodies may be immobilized on an appropriate support or may be included in a kit additionally comprising a support capable of immobilizing the antibodies thereon. Examples of such support that can be used include: synthetic resins capable of adsorbing proteins thereon, such as polyethylene, polypropylene, polybutylene, polystyrene, polymethacrylate, and polyacrylamide; supports made of glass, nitrocellulose, cellulose, and agarose; and supports in a gel state. The form of the support is not particularly limited. The support may be provided in the form of microparticles such as microspheres or beads (e.g., "Latex" beads), a tube (inside wall) such as a microcentrifuge, a microtiter plate (well), or the like.

The present invention also provides a kit for diagnosing a neurodevelopmental disorder or psychiatric disorder accompanied by an abnormality in oxytocin system based on a mutation in CD38 gene. The kit comprises probes capable of detecting substitution of thymine for cytosine at nucleotide No. 4693 of CD38 gene of SEQ ID NO: 1, primers for amplifying a vicinity of the region, etc.

The kit of the present invention may optionally comprise, in addition to the components above, other components necessary for carrying out the present invention, such as reagents for detecting labels, reaction buffer solutions, enzymes, and substrates.

EXAMPLES

Hereafter, the present invention is described in more detail with reference to Examples. However, the present invention is not limited to these Examples.

Example 1

1. Preparation of CD38−/− Mice (Homozygous CD38 Gene-Deficient Mice)

Homozygous CD38 gene-deficient mice (CD38−/− mice) prepared as shown below according to a method by Kato et al. (Tohoku University) (J. Biol. Chem. 274, 1869-1872 (1999)) were kindly provided by Tohoku University, who has previously achieved great result in studies of a CD38/cyclic ADP ribose signaling system, and used in experiments.

(1) Preparation of Targeting Vector

A BamHI-BamHI fragment of 15 kb in length containing exon 1 of mouse AB016868 registered in GenBank was cloned from TT2 embryonic stem cells. This fragment was ligated with BamHI-digested ends of loxP and further with a PKG-1 promoter, a neomycin resistance gene, and a diphtheria toxin A fragment to prepare pCD38-loxP-DTA.

(2) Introduction of Targeting Vector into Mouse ES Cells

The targeting vector pCD38-loxP-DTA was digested at NotI sites and introduced into TT2 stem cells. Neomycin-resistant cells were selected and screened for deficient cells based on CD38 mRNA and CD38 protein expression patterns.

(3) Establishment of CD38−/− Mice

The CD38-deficient stem cells were inserted into embryonic cells from ICR mice at an 8-cell stage to establish chimeric mice. A plasmid containing Cre was introduced into male pronuclei of fertilized oocytes from mice obtained by crossing between the chimeric mice (male) and (C57B1/6J× DBA) F1 mice (female). Some of the newborn mice (F1) obtained from the fertilized oocytes were demonstrated to have CD38 exon 1 deletion. These mice having CD38 exon 1 deletion were backcrossed to ICR mice to obtain heterozygous mice, which were in turn intercrossed to obtain CD38−/− and wild-type mice. These mice were used in experiments.

2. Behavior Abnormalities of CD38−/− Mice (1) Spontaneous Motility
Test Method
According to a previously described method (Matsuoka, Y. et al. Proc. Natl. Acad. Sci. USA. 102, 16066-16071 (2005)), each mouse was placed in a transparent acryl cage (25×30×18 cm), and its motion was measured at 5-minute intervals for 60 minutes in total using an infrared sensor (NS-AS01; Neuroscience Idea., Osaka, Japan).

Results

The CD38−/− mice exhibited significantly higher motility than that of the wild-type littermates (wild-type (N=11), CD38−/− (N=8)) (FIG. 1) and had no or little detectable abnormality in mental activities, such as anxiety or fear.

(2) Maternal Behaviors of Postpartum Female Mice

Test Method

Figure 2:
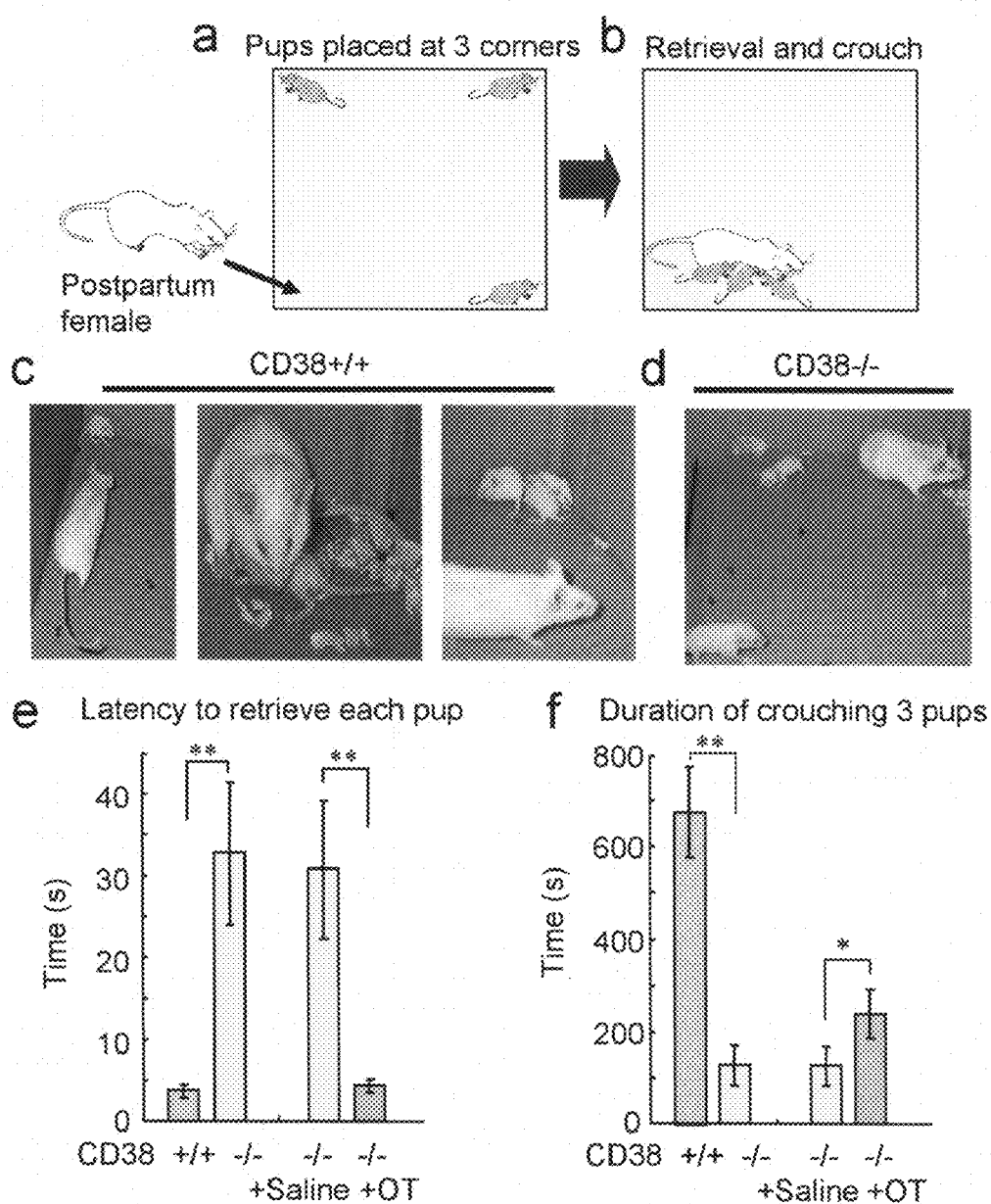
FIG. 2 shows maternal behaviors of wild-type and CD38−/− mice (FIGS. 2a and 2b: summary of an experimental method, FIG. 2c: wild-type mice, FIG. 2d: CD38−/− mice, FIG. 2e: latency to retrieve each pup, FIG. 2f: duration of crouching over pups, **p<0.01, *p<0.05).
Figure 6:
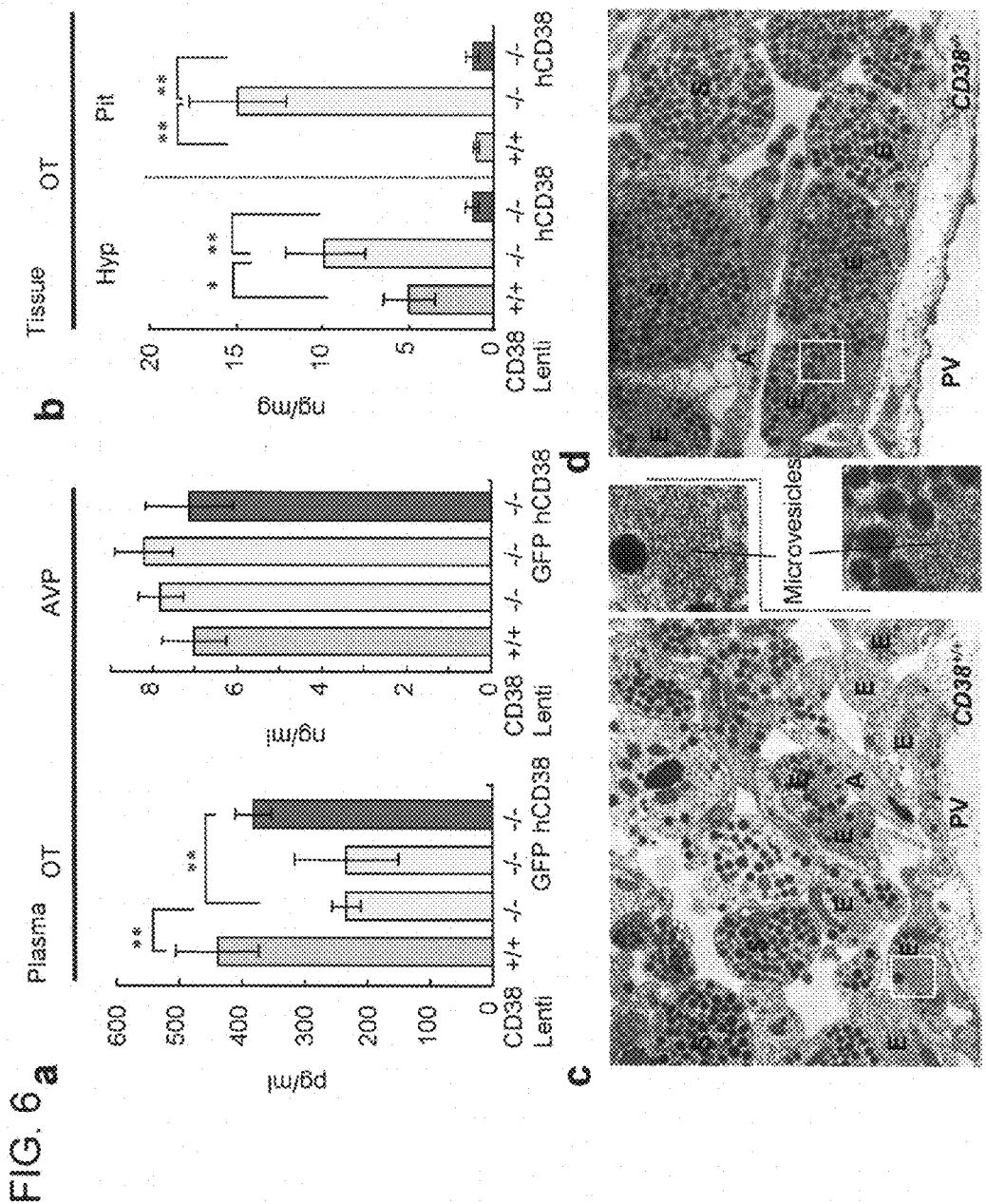
FIG. 6 shows histological/biochemical examination results of wild-type and CD38−/− mice (FIG. 6a: plasma oxytocin (OT) and vasopressin (AVP) concentrations, FIG. 6b: tissue oxytocin (OT) and vasopressin (AVP) concentrations, FIG. 6c: electron micrograph of a wild-type mouse pituitary slice, FIG. 6d: electron micrograph of a CD38−/− pituitary slice).

As shown in FIGS. 2a to 2b, 6- to 14-day-old pups were isolated from postpartum female mice (wild-type (N=6), CD38−/− (N=10)) for 10 minutes. Then, each mother mouse was put back at a corner of a cage, and the pups were placed at remaining 3 corners. In this state, behaviors of the mother mouse were observed. A latency to retrieve each pup and a duration of crouching over 3 pups were also measured.

Results

The wild-type mice retrieved all the pups in an exceedingly short time and crouched over the retrieved pups for a long time for nursing (FIGS. 2c, 2e, and 2f). By contrast, the CD38−/− mice required a long time for retrieving the pups and crouched over the pups for a shorter time than that of the wild-type mice, showing an evident abnormality in maternal behaviors (FIGS. 2d, 2e, and 2f. Thus, the CD38−/− mice exhibited an evident abnormality in their child-care activities (maternal behaviors).

3. Social Memory of Male Mice

Test Method

Figure 3:
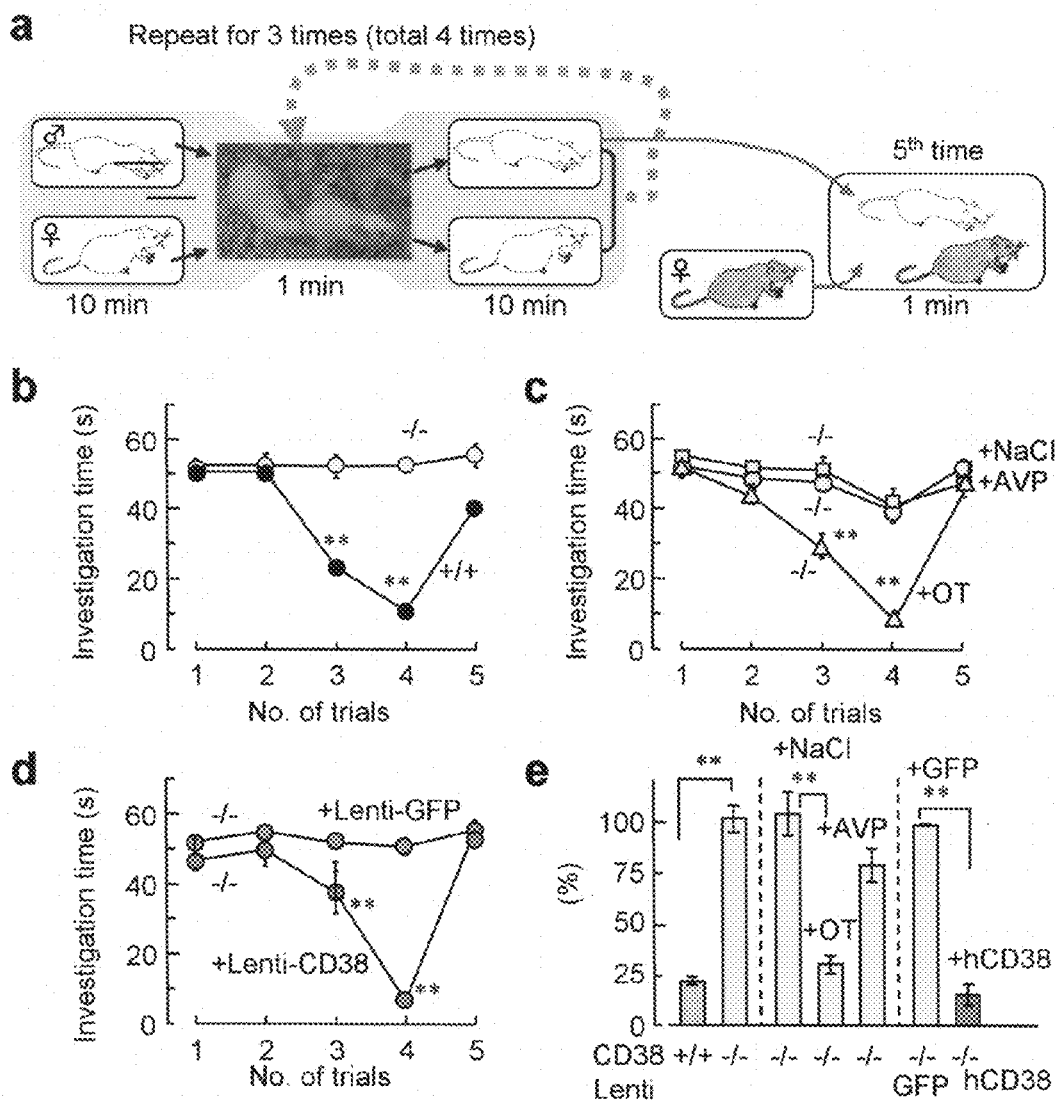
FIG. 3 shows social memories of wild-type and CD38−/− mice (FIG. 3a: summary of an experimental method, FIG. 3b: olfactory investigation time, FIG. 3c: olfactory investigation time after oxytocin (OT), vasopressin (AVP), or saline (NaCl: control) administration, FIG. 3d: olfactory investigation time after introduction of CD38 gene or GFP, FIG. 3e: 4th olfactory investigation time relative to 1st time (%)).
Figure 7:
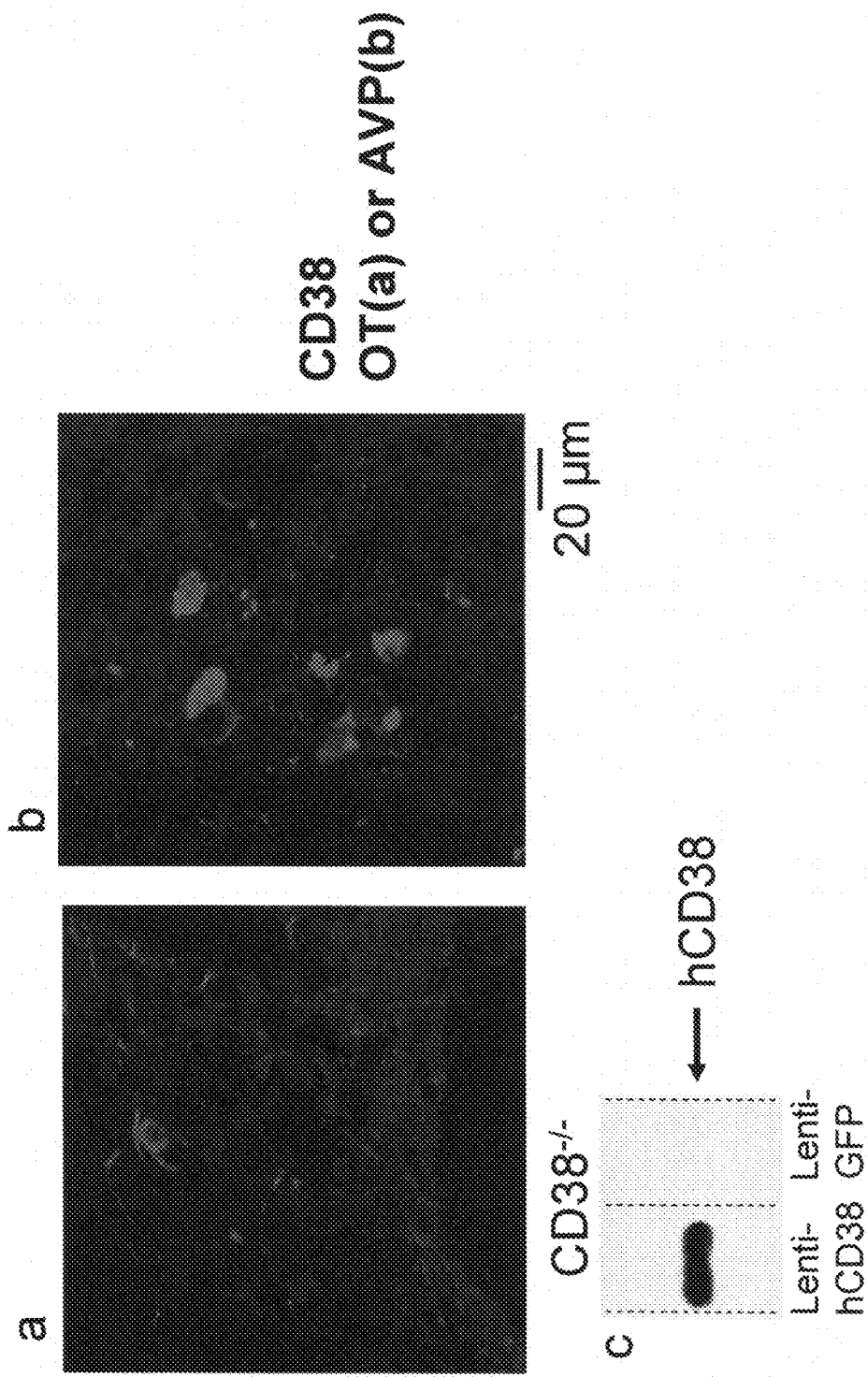
FIG. 7 shows CD38 expression in virus-treated CD38−/− mice (FIGS. 7a and 7b: immunostaining of CD38 and oxytocin (OT) or vasopressin (AVP) in hypothalamus after CD38 gene introduction, FIG. 7c: western blot analysis of posterior pituitary after CD38 gene or GFP introduction).

In general, a male mouse, when encountering with a same female mouse repetitively or for a long time, exhibits a decline in olfactory investigation for identifying the mate. As shown in FIGS. 3, 7- to 9-week-old male mice (N=10 per group) were allowed to encounter with same female mice for 1 minute and reencounter with them after a 10-minute interval, and this procedure was repeated 3 times (4 encounters in total). Subsequently, the male mice were allowed to encounter with new female mice for 1 minute. Their behaviors were video-recorded, and the olfactory investigation time was measured. In this context, each mouse had been housed in a cage for 7 to 10 days before the onset of the test to establish a home-cage territory.

Results

Wild-type mice exhibited a decline in olfactory investigation (time) when encountering with same female mice repetitively (4 times) and showed, when encountering with new female mice, a same level of olfactory investigation as that of the first encounter with the first mice (FIG. 3b). However, young male CD38−/− mice exhibited no decline in olfactory investigation even when encountering with same female mice repetitively (4 times) and exhibited similar olfactory investigation even in the encounter with new female mice (FIG. 3b).

4. Olfactory Function Test

Test Method

To confirm whether the failure of decline in olfactory investigation shown in the preceding paragraph was attributed to abnormal olfactory function, nonsupplemented water and isovaleric acid-containing drinking water were prepared and both are placed in a breeding cage, and the amount of each of the waters drunk by mice was measured for 2 to 4 days and compared. A preference ratio was determined from the amounts of the waters consumed.

Results

Figure 4:
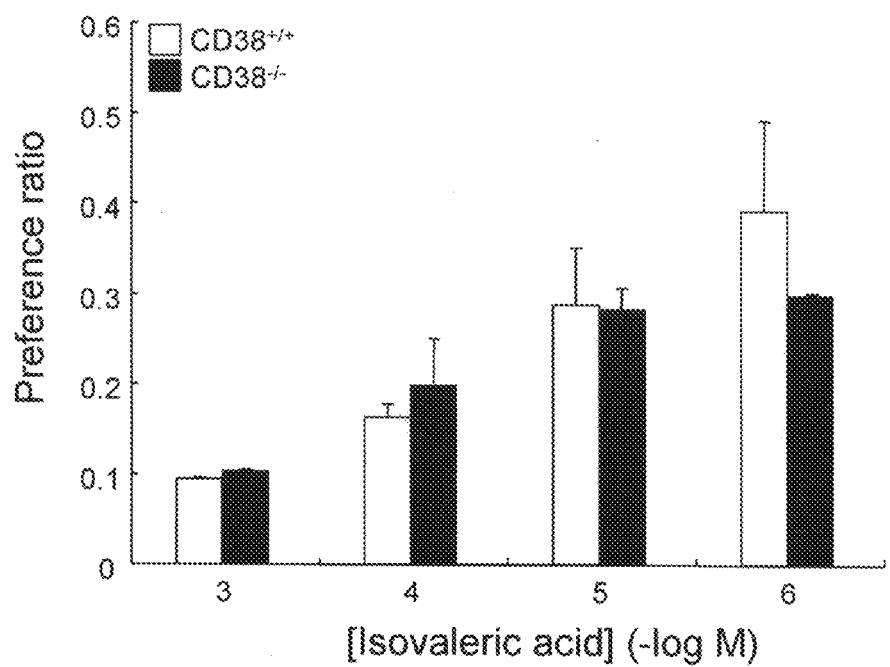
FIG. 4 shows olfactory functions (preference ratio: in the presence of isovaleric acid-containing drinking water and nonsupplemented normal water, the ratio of avoiding the isovaleric acid solution and drinking the normal water) of wild-type and CD38−/− mice.

No significant difference was observed in preference ratio between the CD38−/− and wild-type mice (FIG. 4). This result demonstrated that the abnormal social memory found in the CD38−/− mice is not attributed to olfactory abnormality.

5. Passive Avoidance Test

Test Method

To examine whether the abnormal olfactory investigation was due to general cognitive impairment, a passive avoidance test was conducted for examining learning/memory and behavioral suppression after punishment. A test zone is composed of dark and light boxes, and mice are punished by a weak electric shock from the floor when entering the dark box. First, mice were placed in the light box. When the gate of the dark box is opened, the mice enter the dark box since they prefer a dark place. However, the mice entering the dark box suffers from an electric shock. This procedure was performed 4 times to train the mice. On the next day, the mice were placed in the light box in the same way, and the gate of the dark box was opened. This procedure was performed repetitively. Mice that remember the training hesitate to enter the dark box and enter after a longer latency. Mice were regarded as being normal when they did not enter the dark box for 300 seconds.

Results

Figure 5:
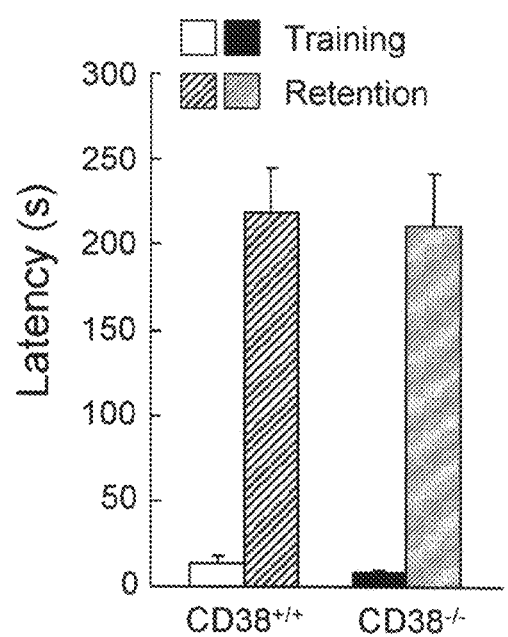
FIG. 5 shows passive avoidance test results of wild-type and CD38−/− mice.

No difference was observed in passive avoidance test between the CD38−/− and wild-type mice (FIG. 5). This result demonstrated that the CD38−/− mice only exhibit reduction in social memory, not general cognitive impairment.

6. Histological/Biochemical Examinations of CD38−/− Mice

Test Method

Immunoassay: Blood and tissues were isolated on the day before the test, and examinations were conducted according to a manufacturer's protocol of a kit (Assay Designs, Inc. Ann Arbor, Mich.). Electron microscopy: Mice were anesthetized with Nembutal and fixed by cardiac perfusion (2% glutaraldehyde, 2% TEA, and 0.1 M phosphate buffer). The tissue was fixed with 2% $OsO_4$ solution and observed using an electron microscope manufactured by JEOL Ltd.

Results

When plasma oxytocin concentrations were measured, the CD38−/− mice exhibited significantly lower values than those of the wild-type mice (FIG. 6a). However, the CD38−/− mice exhibited higher hypothalamic and pituitary oxytocin levels than those of the wild-type mice (FIG. 6b). Little difference was observed between the CD38−/− and wild-type mice in the plasma or tissue concentration of vasopressin, which is also a pituitary hormone (FIG. 6a). When the pituitary gland was analyzed under an electron microscope, the wild-type mice had a small amount of oxytocin-secretion vesicles (dense core vesicles) in nerve terminals (FIG. 6c). On the other hand, the CD38−/− mice were confirmed to have a large amount of such dense core vesicles accumulated in nerve terminals (FIG. 6d). This suggested that the decreased plasma oxytocin concentrations in the CD38−/− mice are due to abnormality in oxytocin release, not in oxytocin synthesis or vesicular uptake (FIG. 6d).

7. Recovery from Behavior Abnormalities by Oxytocin Administration or CD38 Introduction If the decreased plasma oxytocin concentrations cause the behavior abnormalities, then the CD38−/− mice should recover from the behavior abnormalities by supplimentation of oxytocin thereto. Thus, observation was made to confirm whether the CD38−/− mice recovered from the abnormal maternal behaviors and social memory by subcutaneous administration of oxytocin or by introduction of CD38 gene using a lentivirus vector.

(1) Subcutaneous Administration of Oxytocin

Test Method

According to a previously described method (Boccia, M. M., et al., Neurobiol. Learn. Memory 69, 136-146 (1998)), oxytocin (OT) or vasopressin (AVP) dissolved in 0.05 M acetic acid was adjusted to 0.01 μM with saline, and this solution was subcutaneously administered once at a dose of 1 to 10 ng/kg body weight ml to the postpartum female CD38−/− mice (N=6 to 8) described above and young male mice (N=10 per group).

Results

The postpartum female CD38−/− mice recovered to same levels of maternal behaviors as those of the wild-type mice by oxytocin administration (FIGS. 2e and 2f. Moreover, the young male mice recovered a social memory (FIG. 3c). By contrast, vasopressin administration caused no detectable change (FIG. 3c). Additionally, the wild-type mice exhibited no change by oxytocin or vasopressin administration.

(2) Introduction of CD38 Gene

Test Method

According to a previous report (Brain Res. 2006 Apr. 12; 1082 (1): 11-22), a VSV-G pseudo-type lentivirus vector was prepared in which a human CD38 gene (Takasawa, S. et al., J. Biol. Chem. 268, 26052-26054 (1993)) or GFP is placed under the control of an MSCV promoter (lenti-hCD38 or lenti-GFP: these virus vectors show expression in a manner selective for hypothalamus or pituitary gland). These vectors were mixed at a 1:1 ratio to prepare each virus suspension having a concentration of 360000 ng of p24/ml. These virus suspensions were administered to third ventricles of 6- to 8-week-old male mice. Two weeks after the administration, the mice were used in a social memory test.

Results

After 2 weeks, the mice that received lenti-hCD38 exhibited expression and immunoreaction of human CD38 in hypothalamus and pituitary gland, while the mice that received lenti-GFP exhibited no immunoreaction specific for human CD38 (FIG. 7). In the mice that received the lenti-hCD38, the low plasma level and high tissue level of oxytocin were reversed by the lenti-hCD38 introduction, while the mice that received lenti-GFP exhibited no change (FIGS. 6a and 6b). No change was observed in plasma level (FIG. 6a) and tissue level of vasopressin.

The male CD38−/− mice that received lenti-hCD38 recovered a social memory. Specifically, their olfactory investigation was declined as a number of encounters with same females increased, and the male mice recovered olfactory investigation by an encounter with new female mice (FIG. 3d). This recovery brought by lenti-hCD38 expression was comparable to that brought by subcutaneous administration of oxytocin (FIG. 3e).

8. Test Method for Expression and Enzymatic Activity of CD38

1) ADP-Ribosyl Cyclase Activity

An ADP-ribosyl cyclase activity was determined according to a previous report (Higashida, H. et al., J. Biol. Chem. 274, 33348-33354 (1999)). Specifically, an amount of cyclic GDP-ribose (cGDPR) produced using nicotinamide guanine dinucleotide (NGD) as an enzyme substrate was determined using a fluorescence spectrometer. An excitation wavelength of 349 nm and a measurement wavelength of 499 nm were used.

2) cADPR Level

A cADPR level was measured by an enzymatic recycling method according to a previous report (Graeff, R. & Lee, H. C., Biochem. J. 361, 379-384 (2002)) using nucleotides extracted from tissues with 0.6 M perchloric acid at 4° C.

3) Isolation of Hypothalamic Cells and Pituitary Nerve Terminals

Cell bodies of hypothalamic neurons and nerve terminals were isolated according to a previously described method (OuYang, W., et al., Brain Res. 1024, 203-21.1 (2004)), then washed with a Locke solution, and homogenized in a solution containing sucrose, 270; HEPES-Tris, 10; and K-EGTA, 0.01 (in mM, pH 7.25). The homogenates were transferred to Petri dishies and left standing for 5 to 8 minutes.

Results

Figure 8:
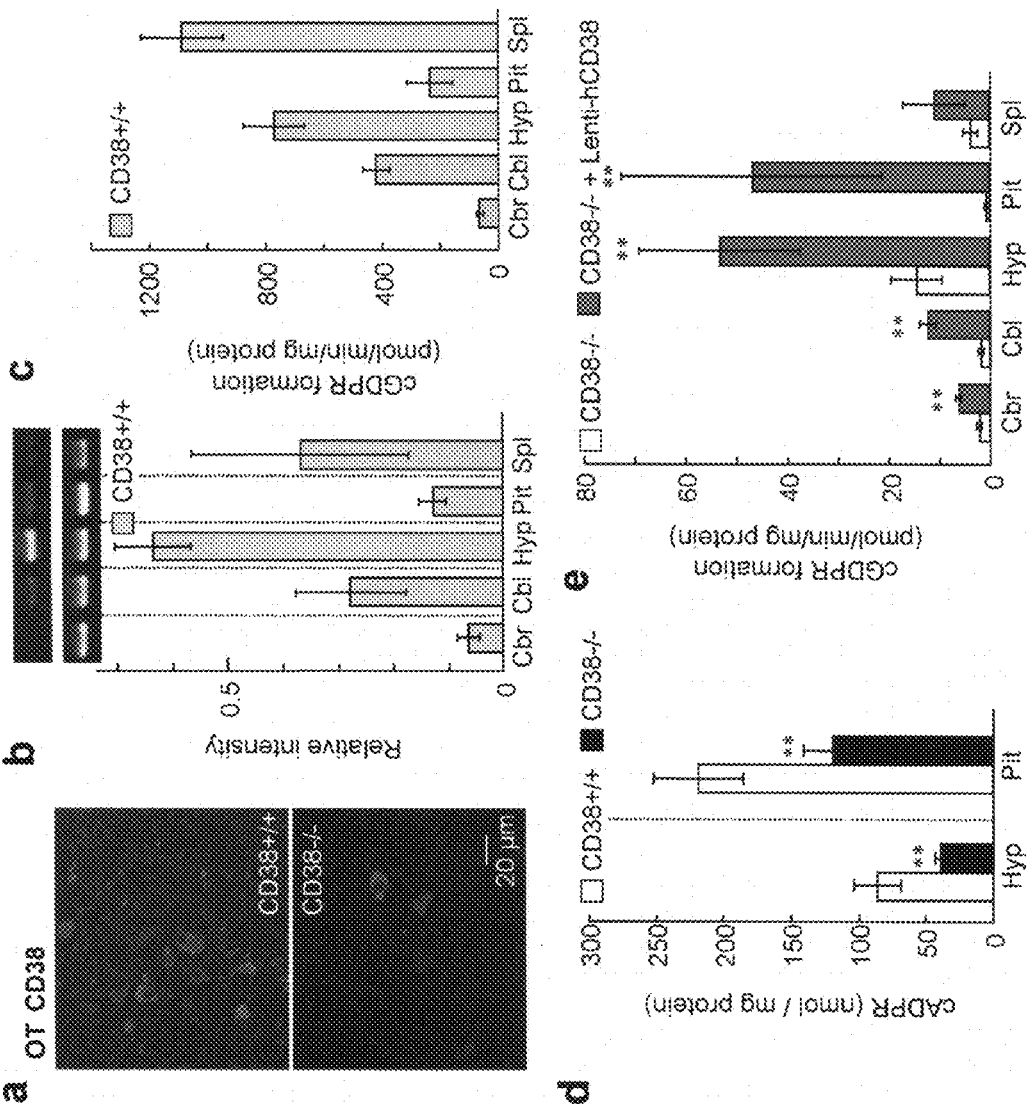
FIG. 8 shows expression and enzymatic activity of CD38 in wild-type and CD38−/− mice.

The brain tissues isolated from the CD38−/− mice exhibited ADP-ribosyl cyclase activity remarkably reduced as CD38 expression levels decreased. The immunohistological analysis of a hypothalamic paraventricular region and other examinations demonstrated this phenotypic change (FIG. 8).

Figure 9:
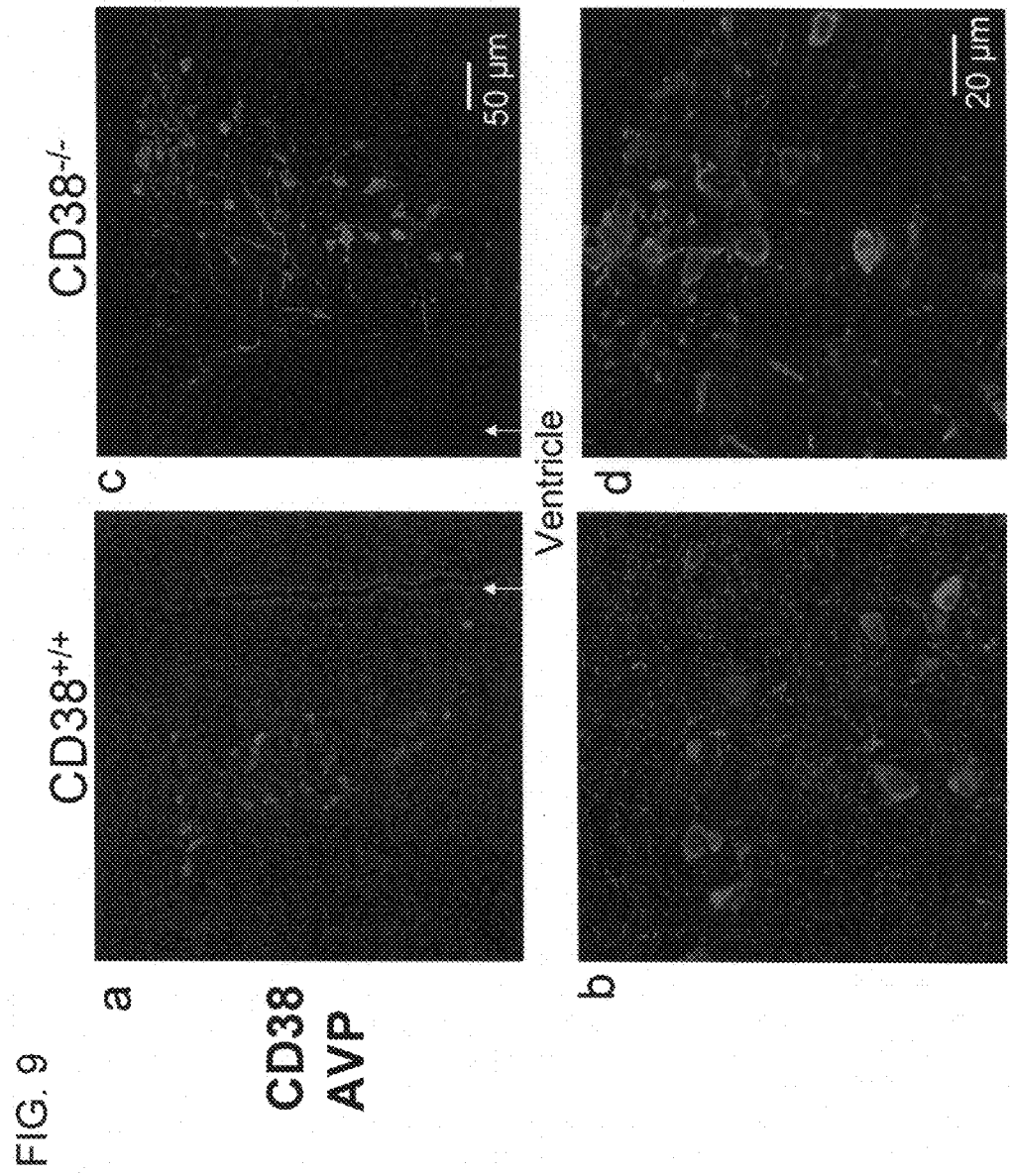
FIG. 9 shows immunochemical analyses of CD38 and AVP in wild-type and CD38−/− mice. CD38 is stained red with goat anti-mouse CD38 polyclonal antibodies, and AVP is stained green with rabbit anti-AVP antibodies.

In the wild-type mice, CD38 immunoreaction was observed as dots on or outside of oxytocin-expressing and/or vasopressin-expressing nerves, while the CD38−/− mice had only background levels of the immunoreaction (FIGS. 8a and 9). The wild-type mice had a very high CD38 mRNA level in hypothalamic region but low in posterior pituitary (FIG. 8b). This result was well consistent with the result of measurement of ADP-ribosyl cyclase activity based on amounts of cGDPR produced from NGD+ (FIG. 8c).

The CD38−/− mice exhibited an exceedingly low ADP-ribosyl cyclase activity in both of hypothalamus and posterior pituitary (FIG. 8e), which was consistent with the decreased amount of cADPR (FIG. 8d).

The CD38−/− mice partially recovered from the reduced ADP-ribosyl cyclase activity by introduction of human CD38 gene (FIG. 8e).

9. Oxytocin Release and $Ca^{2+}$ Concentration (In Vitro)

Test Method

Oxytocin Release:

Isolated cells and nerve terminals were left standing for 6 hours, and then, an experiment was started. The specimens were perfused for 45 minutes, and the perfusate was collected at last 5-minute intervals three times in total for control concentration measurement. Subsequently, the specimens were perfused for additional 5 minutes with Locke solution containing 70 mmol of KC1, and oxytocin concentrations in the obtained perfusates were determined using an oxytocin determination kit and considered as concentrations of oxytocin released by depolarization stimulation.

Intracellular Calcium:

The cells were incubated with Oregon Green for 1 hour to incorporate the dye into the cells. Subsequently, a fluorescence intensity of the cells was measured using an excitation wavelength of 485 nm and a filter of 538 nm. A fluorescence microspectrophotometer and a condenser with an ARGUS-50 CCD camera were used for the measurement.

Results

Figure 10:
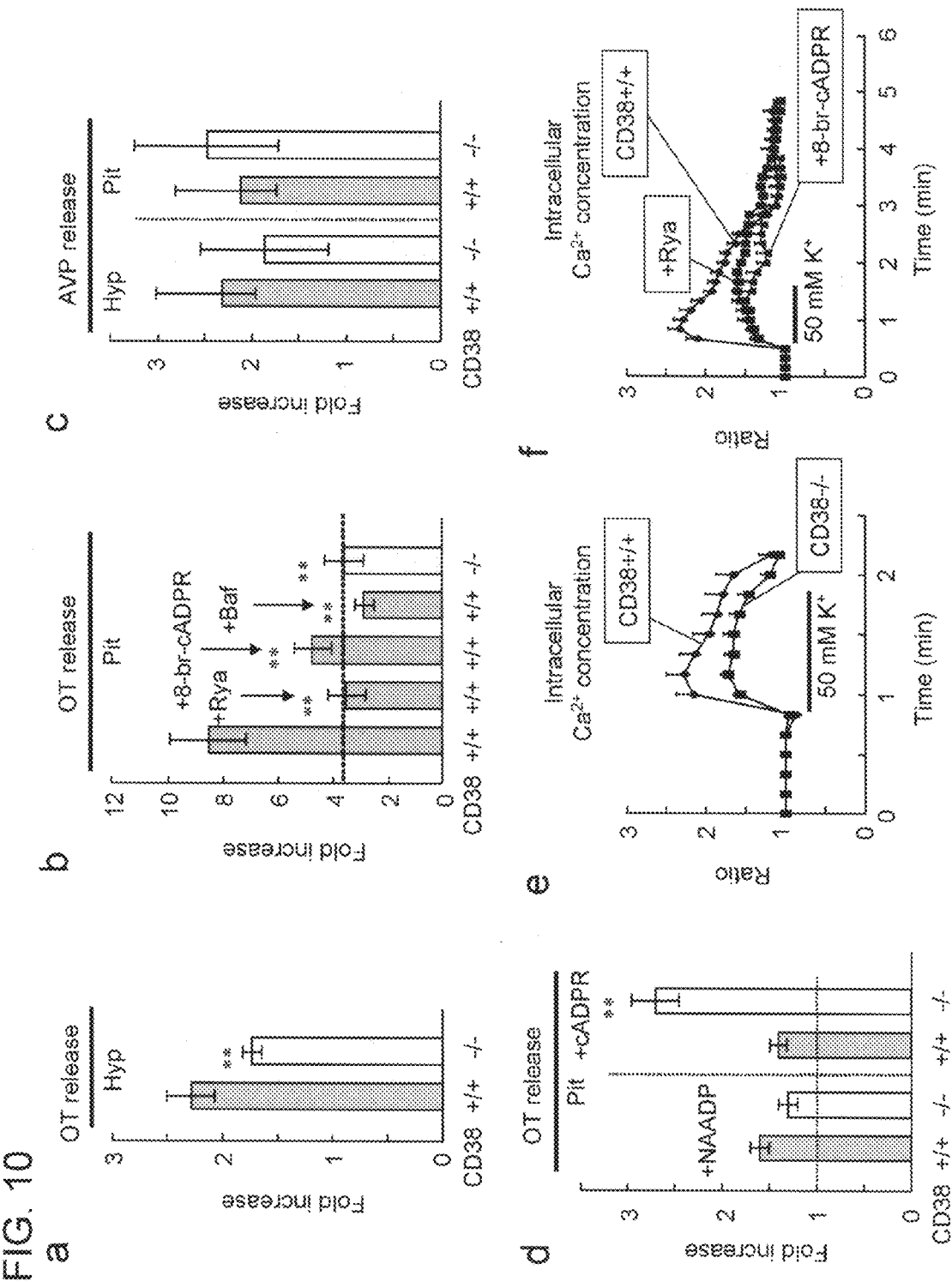
FIG. 10 shows results of examining influences of various antagonists on oxytocin or vasopressin release or on change in intracellular calcium concentration in wild-type and CD38−/− mice.

In the wild-type mice, depolarization with a high concentration of potassium increased oxytocin release from the isolated hypothalamic nerves 2-fold or more (FIG. 10a) and increased the release from the pituitary nerve terminals 8-fold (FIG. 10b). On the other hand, in the CD38−/− mice, both the tissues (particularly remarkably, the pituitary nerves) exhibited lower oxytocin release (FIGS. 10a and 10b), while none of the regions had detectable changes in vasopressin release (FIG. 10c).

Oxytocin release from the pituitary nerve terminals in the wild-type mice was decreased to same levels as those in the CD38−/− mice by treatments with 200 µM ryanodine (ryanodine in this amount acts as a full antagonist for ryanodine receptors), 100 µM 8-bromo-cADPR (antagonist for a ryanodine receptor-binding site of cADPR), and 2 µM bafilomycin (NAADP antagonist) (FIG. 10b).

Figure 11:
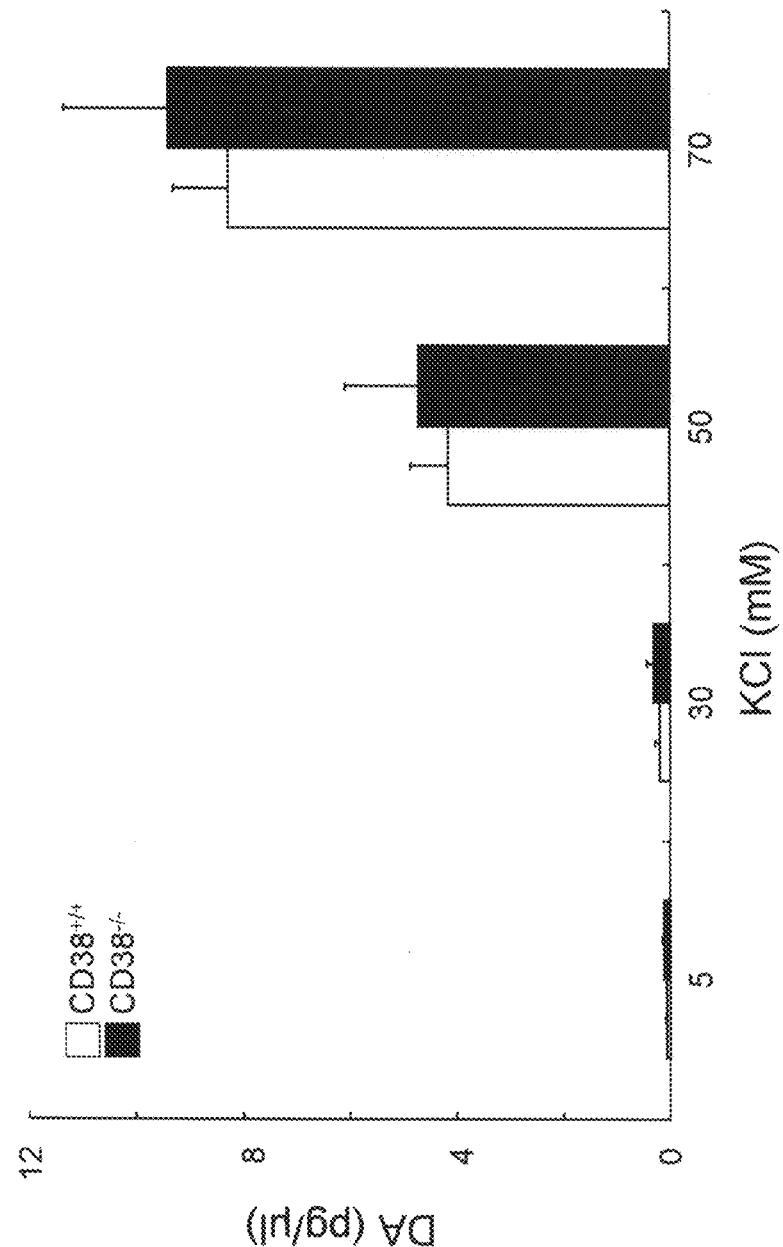
FIG. 11 shows relationships between depolarization with high potassium and dopamine release in wild-type (left columns) and CD38−/− (right columns) mice.

Furthermore, in all the mice initially stimulated with $Ca^{2+}$, oxytocin release from the pituitary nerve terminals was promoted by cADPR (10 µM) and NAADP (100 nM) given outside the cells. Particularly, in the CD38−/− mice, cADPR increased oxytocin release even 2.5-fold (FIG. 10d). This indicates that these metabolites produced via ADP-ribosyl cyclase are essential for oxytocin release and thus indicates that insufficient oxytocin release and decreased plasma oxytocin level in the CD38−/− mice are associated with ADP-ribosyl cyclase activity. In addition, these events did not influence vasopressin release, suggesting that insufficient oxytocin release and decreased plasma oxytocin level do not reflect a general defect in neuronal secretions. No influence on depolarization-induced dopamine release in corpus striata in the CD38−/− mice also supported this hypothesis (FIG. 11).

Oxytocin release from the hypothalamic cells is triggered by an increase in intracellular calcium concentration due to entry of extracellular calcium via voltage-dependent calcium channels associated with a repetitive generation of action potentials. It has been reported that an increase in $Ca^{2+}$ concentration mediated by thapsigargin-sensitive $IP_3$ and slight $Ca^{2+}$ release ($Ca^{2+}$ syntillas) from ryanodine receptors in hypothalamic nerve terminals are observed in somatic cells and dendritic cells (e.g., Ludwig, M. & Leng, G. Nat. Rev. Neurosci. 7, 126-136 (2006)). Transient increase in $Ca^{2+}$ concentration in isolated nerve terminals was examined using a $Ca^{2+}$-sensitive dye Oregon Green. As a result, incubation in the presence of 50 mM KCl increased intracellular $Ca^{2+}$ concentration to 220% in the wild-type mice but only to 160% in the CD38−/− mice (FIG. 10e). Interestingly, the remarkable increase in intracellular $Ca^{2+}$ concentration in the wild-type mice was significantly inhibited in the presence of ryanodine or 8-bromo-cADPR (FIG. 10f).

10. Conclusion

These results demonstrated that CD38 function-deficient mice exhibit behavior abnormalities (abnormal maternal behaviors and social memory) very similar to autism, and these behavior abnormalities are due to failure of oxytocin release. It was further suggested that CD38 specifically inhibits oxytocin release via an increase in intracellular $Ca^{2+}$ concentration mediated by a cADPR and NAADP-ryanodine receptor system. This fact indicates that a therapeutic drug for a neurodevelopmental disorder or psychiatric disorder accompanied by an abnormality in oxytocin system, including autism, can be developed by screening for, for example: a compound that allows recovery from a decreased expression level, decreased activity, or localization of CD38; a compound that increases amounts of cADPR and NAADP which are second messengers in an oxytocin release system regulated by CD38; a compound that increases an intracellular calcium concentration in such a system; or a compound that directly increases oxytocin release.

Example 2

(1) Subjects

Subjects were 11 autistic individuals who visited Kanazawa University Hospital in 2006 and 49 healthy individuals. They consented to be registered in the study and presented a written informed consent.

(2) RT-PCR-RFLP and Sequencing

Erythrocyte components were removed from peripheral blood collected from each of the autistic and healthy individuals, and precipitated leucocytes were separated therefrom. From the leucocytes, RNA was extracted according to a standard method. The obtained RNA samples were diluted by addition of TRIzol reagent to prepare RT-PCR samples.

RT-PCR was performed using an RT-PCR kit manufactured by Qiagen. Specifically, the RNA sample obtained from each subject was used as a template to amplify each CD38 exon region using primers shown below.

TABLE 1

| | Sequence | | Size of amplification product |
|---|---|---|---|
| exon 1 | Forward: 5'-CTCCTGCCGGCCTCATCTTC-3' | (SEQ ID NO: 5) | 329 bp |
| | Reverse: 5'-GCCCTGCTGTCCCCGCAGTG-3' | (SEQ ID NO: 6) | |
| exon 2 | Forward: 5'-GGCATATAATAGATGCTTCC-3' | (SEQ ID NO: 7) | 304 bp |
| | Reverse: 5'-TGGACCTATGAATTGTTACC-3' | (SEQ ID NO: 8) | |
| exon 3 | Forward: 5'-GACATGCTAAATTGATCTCAG-3' | (SEQ ID NO: 9) | 248 bp |
| | Reverse: 5'-CAGCAGAAGTCACTCTGTTC-3' | (SEQ ID NO: 10) | |
| exon 4 | Forward: 5'-TCCACTATGACTGAACAGCC-3' | (SEQ ID NO: 11) | 244 bp |
| | Reverse: 5'-AGCACTGACTGAGTAACGTC-3' | (SEQ ID NO: 12) | |
| exon 5 | Forward: 5'-CTTAACCAGCTATTGCTAAG-3' | (SEQ ID NO: 13) | 223 bp |
| | Reverse: 5'-ACTGTGATATTTGCAACAGG-3' | (SEQ ID NO: 14) | |
| exon 6 | Forward: 5'-TCTGCCTGCTGGTTGTTGAG-3' | (SEQ ID NO: 15) | 272 bp |
| | Reverse: 5'-TCCTGAGTCAATTTGTTCCC-3' | (SEQ ID NO: 16) | |

TABLE 1-continued

| Sequence | | | Size of amplification product |
|---|---|---|---|
| exon 7 Forward: | 5'-CCTTGTCCAGGGCGTGCTAC-3' | (SEQ ID NO: 17) | 258 bp |
| Reverse: | 5'-AAGCTCAGAGGAGGCTAAGG-3' | (SEQ ID NO: 18) | |
| exon 8 Forward: | 5'-AGCGAATTGGACGACAGATG-3' | (SEQ ID NO: 19) | 250 bp |
| Reverse: | 5'-CATTGACCTTATTGTGGAGG-3' | (SEQ ID NO: 20) | |

PCR was performed under conditions comprising denaturation at 94° C. for 5 minutes and 30 cycles of denaturation (94° C.×0.5 min.), annealing (50° C.×1 min.), and extension (72° C.×25 min.), followed by final extension (72° C.×10 min.).

Obtained PCR products were electrophoresed on agarose gels. As a result, the products of all the exon regions were confirmed in the samples from the 11 autistic individuals to have same sizes as those of predicted products.

These amplification products were cloned according to a standard method and sequenced using ABI PRISM 310 capillary sequencer. As a result, one of these 11 patients was confirmed to have a substitution of thymine (T) for cytosine (C) at position 4693 in exon 3 region (see the sequence shown below). This polymorphism was a newly revealed exon polymorphism involving a substitution of tryptophan for arginine at position 140 in CD38 amino acid sequence of SEQ ID NO: 2. On the other hand, none of the 49 healthy individuals had this substitution.

(SEQ ID NO: 4)
GACATGCTAAATTGATCTCAGTAATAGATTGTATTTATTCTTCCTTAGAT

TCTTCTTTGGAGCAGAATAAAAGATCTGGCCCATCAGTTCACACAGGTCC

AG[C/T]GGGACATGTTCACCCTGGAGGACACGCTGCTAGGCTACCTTGC

TGATGACCTCACATGGTGTGGTGAATTCAACACTTCCAGTGAGGCTCTGG

GCCCTGTGGGATTGCCCAGGGATGTGGAGGGTGAACAGAGTGACTTCTGC

TG

Example 3

1. Introduction of Mutated CD38 Gene

Test Method

According to a previously described method (Brain Res. 2006 Apr. 12; 1082 (1): 11-22), a VSV-G pseudo-type lentivirus vector was prepared in which a human CD38 gene (Takasawa, S. et al., J. Biol. Chem. 268, 26052-26054 (1993)), a mutated human CD38 gene (Yagui, K. et al., Diabetologia. 1998 September; 41 (9): 1024-1028), or GFP is placed under the control of an MSCV promoter (lenti-hCD38, lenti-R140W-hCD38, or lenti-GFP: these virus vectors show expression in a manner selective for hypothalamus or pituitary gland). The mutated human CD38 gene used in the examinations has a substitution of tryptophan for arginine at position 140 in CD38 amino acid sequence of SEQ ID NO: 2. Each virus suspension thereof was administered to third ventricles of 6- to 8-week-old male mice. Two weeks after the administration, the mice were used in a social memory test.

Results

Figure 12:
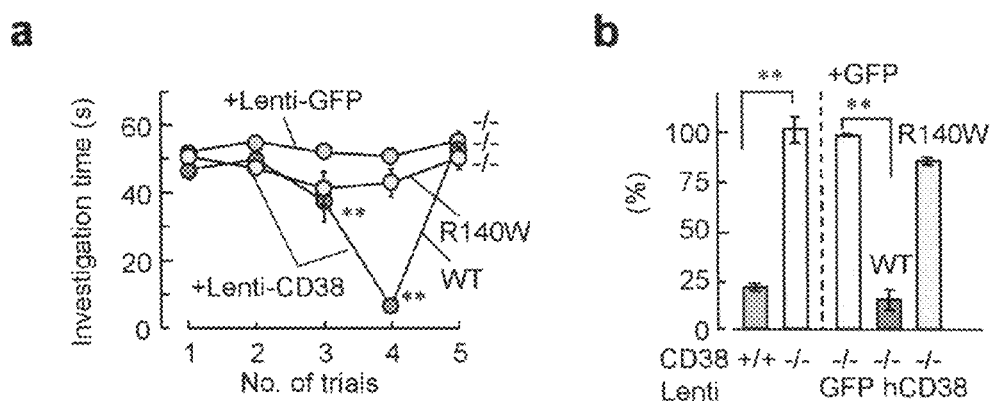
FIG. 12 shows social memories of wild-type and CD38−/− mice.

The male CD38−/− mice that received lenti-hCD38 recovered a social memory. Specifically, their olfactory investigation was declined as a number of encounters with same females increased, and the male mice recovered olfactory investigation by an encounter with new female mice (FIG. 12a). This recovery brought by lenti-hCD38 expression was comparable to that brought in the CD38−/− and wild-type mice by subcutaneous administration of oxytocin (FIG. 12b). Furthermore, to examine an importance of CD38 enzymatic activity for recovery of a social memory, a test was conducted using the mutated human CD38. This mutated CD38 has been known to be found in human diabetes and have about ⅓ of normal ADP-ribosyl cyclase activity. The mutated CD38 was expressed in hypothalamus by lenti-R140W-hCD38 introduction. The CD38−/− mice did not recover a social memory by the mutated CD38 expression (FIGS. 12a and 12b). Thus, it was suggested that the enzymatic activity of CD38, not the CD38 molecule itself, plays an important role in the recovery of social memory, and this mutation probably serves as a cause of behavior abnormalities such as an abnormal social memory.

Example 4

(1) Subjects

Subjects were 29 autistic individuals (3 of them were subjected to family analysis), 201 healthy individuals, and 50 individuals with MR (mental retardation). They consented to be registered in the study and presented a written informed consent.

(2) RT-PCR-RFLP and sequencing

RNA was extracted from peripheral blood leucocytes of each subject according to Example 2, and each CD38 exon region was amplified. Each amplified DNA fragment was sequenced by direct sequencing and subjected to mutation analysis.

Furthermore, family members who presented a consent among the families of 3 out of the autistic individuals were subjected to clinical analysis and polymorphism analysis.

(3) Plasma Oxytocin and Vasopressin Levels

Furthermore, the 29 autistic individuals and the family members of the 3 autistic individuals were subjected to an analysis of plasma oxytocin and vasopressin levels.

Results

Figure 13:
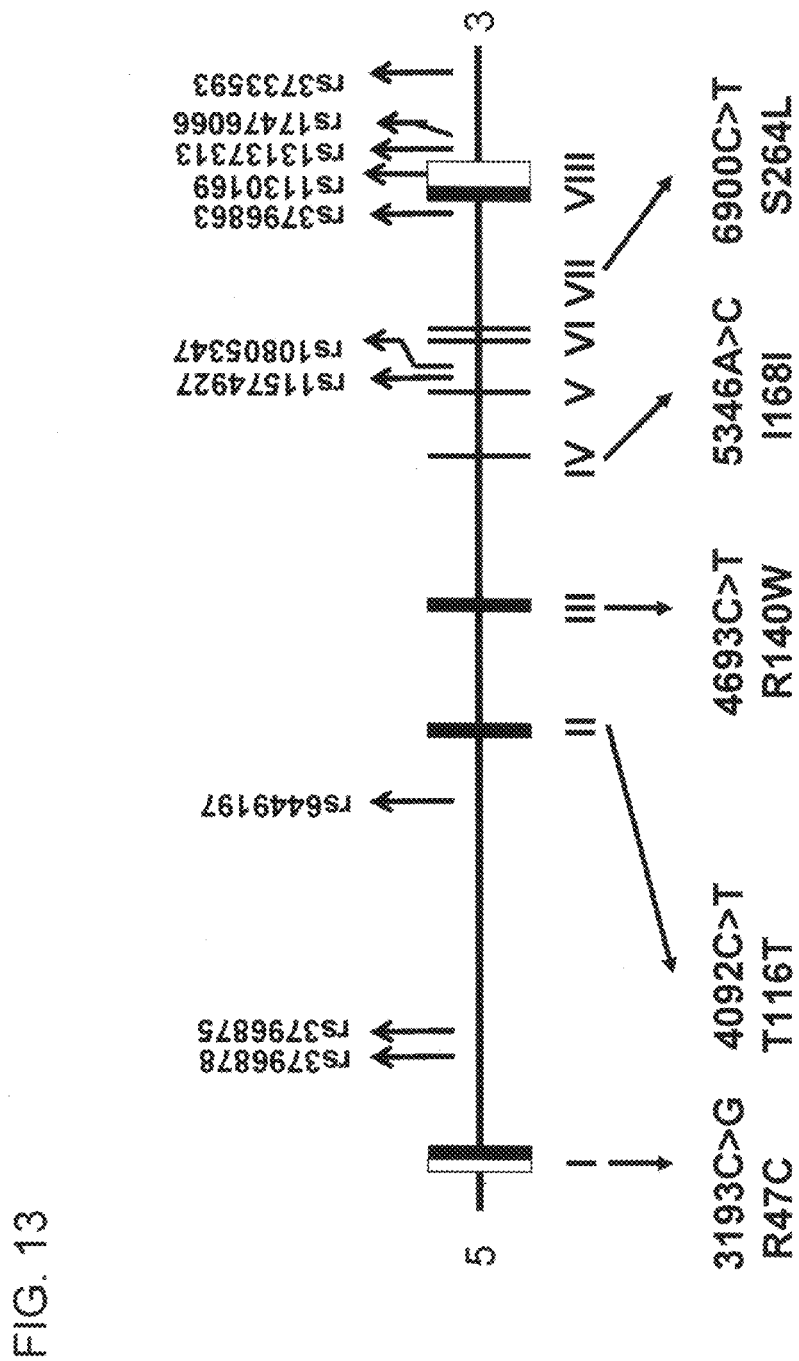
FIG. 13 shows polymorphisms in CD38 gene.

As a result, in exon regions, 5 polymorphisms including the polymorphism at position 4693 in exon 3 region described in Example 2 were identified: 3193C>G (R47C) in exon 1; 4092C>T (T116T) in exon 2; 4693C>T (R140W) in exon 3; 5346A>C (I168I) in exon 4; and 6900C>T (S264L) in exon 7 (FIG. 13).

The polymorphism at position 4693 in exon 3 region (R140W) was observed in 3 out of the 29 autistic individuals (10.3%), only 3 out of the 201 healthy individuals (1.5%), and none of the 50 MR individuals.

Figure 14:
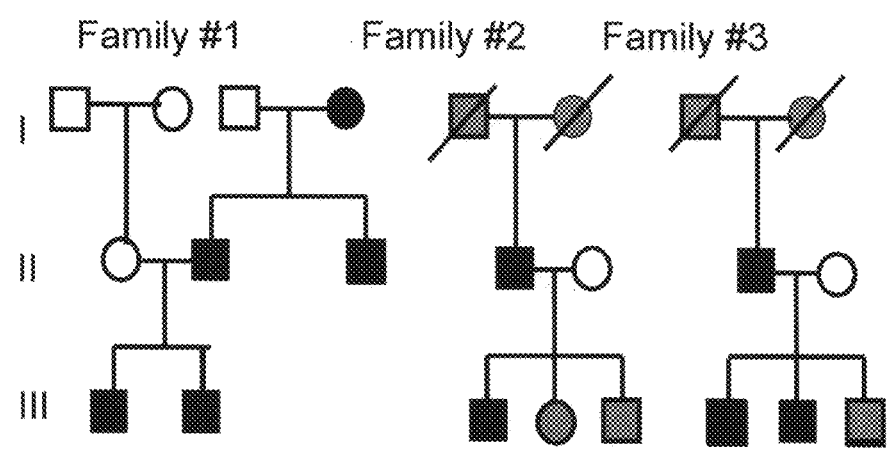
FIG. 14 shows results of investigation of a polymorphism in three families of autistic individuals having a polymorphism at position 4693 in exon 3 region. Filled patterns represent individuals having the polymorphism, and shaded patterns represent individuals not having the polymorphism.

In the family analysis for the 3 autistic individuals having the polymorphism at position 4693 in exon 3 region, 6 out of the 13 individuals (46%) that presented a consent were found to have the same polymorphism (heterozygous in all cases). Moreover, 5 out of the family members having this polymorphism were confirmed to have autism or a high possibility of autism (FIG. 14).

Figure 15:
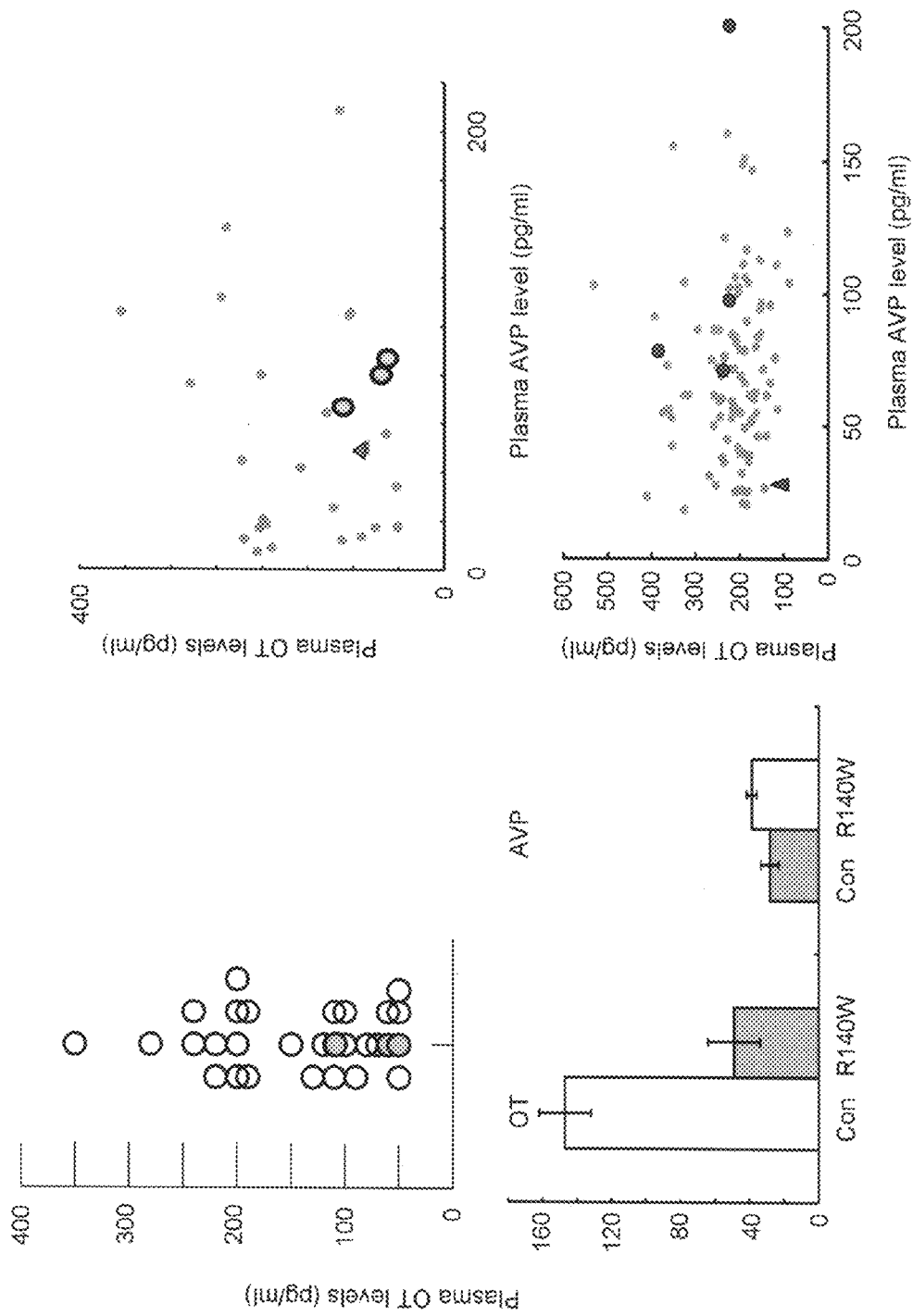
FIG. 15 shows plasma oxytocin (OT) and plasma vasopressin (AVP) levels of 29 autistic individuals including those having a polymorphism at position 4693 in exon 3 region (R140W) and those having no polymorphism at this position (Con).

Of the 29 autistic individuals, those having the polymorphism at position 4693 in exon 3 region and those having no polymorphism at this position significantly differed in plasma oxytocin levels but did not differ in plasma vasopressin levels (FIG. 15).

These results suggested that the polymorphism at position 4693 in exon 3 region (R140W) acts in a genetically dominant manner and highly probably has some relation to autism since the individuals having this polymorphism have significantly lower serum oxytocin levels than those of the individuals not having this polymorphism.

All publications, patents, and patent applications cited herein are incorporated herein by reference in their entirety.

INDUSTRIAL APPLICABILITY

The present invention is useful for early diagnosis or treatment of a neurodevelopmental disorder or psychiatric disorder accompanied by an abnormality in oxytocin, for example, autism, Asperger syndrome, hyperactivity disorder, and learning/memory impairment.

SEQUENCE LISTING

SEQ ID NO: 1: human CD38 complete cds (GenBank Accession NO. D84284)
  n=a, c, g, or t
Description of variation: single-nucleotide replacement of (C) and (T)
SEQ ID NO: 2: human CD38 amino acid sequence
SEQ ID NO: 3: human CD38 exon 3 (positions 4639-4774 in complete cds)
Description of variation: single-nucleotide replacement of (C) and (T)
SEQ ID NO: 4: amplified sequence including human CD38 exon 3
SEQ ID NO: 5: primer
SEQ ID NO: 6: primer
SEQ ID NO: 7: primer
SEQ ID NO: 8: primer
SEQ ID NO: 9: primer
SEQ ID NO: 10: primer
SEQ ID NO: 11: primer
SEQ ID NO: 12: primer
SEQ ID NO: 13: primer
SEQ ID NO: 14: primer
SEQ ID NO: 15: primer
SEQ ID NO: 16: primer
SEQ ID NO: 17: primer
SEQ ID NO: 18: primer
SEQ ID NO: 19: primer
SEQ ID NO: 20: primer

The invention claimed is:

1. A method of determining a predisposition of a human subject to a neurodevelopmental disorder or psychiatric disorder accompanied by an abnormality in an oxytocin system, comprising:
   detecting a mutation in a CD38 gene region in a sample isolated from the human subject, wherein the mutation encodes a substitution of tryptophan for arginine at position 140 in the CD38 amino acid sequence of SEQ ID NO: 2 or a substitution of thymine for cytosine at position 4693 in the CD38 gene of SEQ ID NO: 1.

2. The method according to claim 1, wherein the mutation is a substitution of tryptophan for arginine at position 140 in the CD38 amino acid sequence of SEQ ID NO: 2.

3. The method according to claim 1, wherein the mutation is a substitution of thymine for cytosine at position 4693 in the CD38 gene of SEQ ID NO: 1.

4. The method according to any one of claims 1 to 3, wherein the neurodevelopmental disorder or psychiatric disorder accompanied by an abnormality in the oxytocin system is selected from the group consisting of autism, Asperger syndrome, hyperactivity disorder, and learning/memory impairment.

* * * * *

SEQUENCE LISTING

```
<160> NUMBER OF SEQ ID NOS: 20

<210> SEQ ID NO 1
<211> LENGTH: 8622
<212> TYPE: DNA
<213> ORGANISM: Homo sapiens
<220> FEATURE:
<221> NAME/KEY: misc_feature
<223> OTHER INFORMATION: Inventor: Higashida, Haruhiro
<220> FEATURE:
<221> NAME/KEY: misc_feature
<223> OTHER INFORMATION: human CD38 complete CDS (GenBank D84284)
<220> FEATURE:
<221> NAME/KEY: misc_feature
<222> LOCATION: (3557)..(3656)
<223> OTHER INFORMATION: n is a, c, g, or t
<220> FEATURE:
<221> NAME/KEY: misc_feature
<222> LOCATION: (4323)..(4422)
<223> OTHER INFORMATION: n is a, c, g, or t
<220> FEATURE:
<221> NAME/KEY: variation
<222> LOCATION: (4693)..(4693)
<223> OTHER INFORMATION: Description of variation: single nucleotide
     polymorphism involving replacement of (C) and (T)
<220> FEATURE:
<221> NAME/KEY: misc_feature
<222> LOCATION: (5070)..(5169)
<223> OTHER INFORMATION: n is a, c, g, or t
<220> FEATURE:
<221> NAME/KEY: misc_feature
<222> LOCATION: (5560)..(5659)
<223> OTHER INFORMATION: n is a, c, g, or t
<220> FEATURE:
<221> NAME/KEY: misc_feature
<222> LOCATION: (6113)..(6212)
<223> OTHER INFORMATION: n is a, c, g, or t
<220> FEATURE:
<221> NAME/KEY: misc_feature
```

<222> LOCATION: (7111)..(7210)
<223> OTHER INFORMATION: n is a, c, g, or t

<400> SEQUENCE: 1

| | | | | | |
|---|---|---|---|---|---|
| aagcttatac | ccaagtggct | ccttgatgcc | tcctgttggg | ggtctaatag | acatctcaaa | 60 |
| cttagcacat | caaaaaccaa | attcttgatt | catgcctctt | cccaagacca | aatctacttc | 120 |
| acctcccgtt | ttcccatcac | tgtagattgc | agtgctttcc | ttcctttggt | cagttacaca | 180 |
| aataaaaaat | cttggcatca | tctttgactc | atctctttct | tgcaaatgct | acatccaatt | 240 |
| catcagcaaa | tcctgctgct | gctaccttca | aactctattc | agaatccatc | ttttttttc | 300 |
| tttgccacct | tcattactgc | tactacagcc | attgtaactg | ttctccatcc | ttatcctcct | 360 |
| acaatttatt | cttaatacca | aagccagatt | gatcctttaa | aataatatgc | cagatcaagt | 420 |
| catttggtga | cttgtatggg | taaaaataaa | atgcacacga | atgggttaaa | aataaaatcc | 480 |
| aaaaacaggc | acatagacca | atgaaacaga | atagagatct | cagaaataag | actcacatct | 540 |
| acaaccatct | gatctttgac | agacctgaca | aaaacaagca | atggggaaag | gattccctat | 600 |
| ttaataaatg | gtgctgggaa | aactggctag | ctatacgcag | aaaattgaaa | ctggatccct | 660 |
| tccttacacc | ttttcaaaa | attaactcaa | gatggattaa | agatttaaaa | tgtaaaaccc | 720 |
| aaaactataa | aaaccctaga | agaaaatcta | ggcaatacca | ttcaggacat | aggcatgggc | 780 |
| aaagatttca | taatgaaaat | gtcaaaagca | attccaacaa | aagcgaaaat | gacaaatggg | 840 |
| atccaattaa | actcaggaac | ttctgcacac | cgaaagaaac | tataatcagg | gtgaacagac | 900 |
| aacctacagc | atgggagaac | attttcaaaa | tctatccatc | tgacaaaggt | ctaatatcca | 960 |
| gaatctacaa | ggaacttaaa | ctaatttata | agaaataaac | aaccccatta | aaaagtgggc | 1020 |
| aaaggacatg | aacagatatt | tctcaaaaga | agacatttat | atagccaaca | acatatgaa | 1080 |
| aaaaagctca | acatcattga | tcattagaaa | aatgcaaacc | aaaaccacaa | tgaaatatca | 1140 |
| tctcatgcca | gtcagaatgg | tgatcattaa | aaagtcaata | acaacagat | gctggtgagg | 1200 |
| ttgtggagaa | ataggaacac | ttacactgtt | gatgggagtg | taaattagtt | caaccattgt | 1260 |
| ggaagacagt | atggggattc | ctcaaagatc | tagaaccaga | aataccattt | gacccagcaa | 1320 |
| tctcattact | gggtatatac | ccaaaggaat | ataaatcatt | ctgttataaa | gatacatgca | 1380 |
| tgcatatgtt | cattgtagca | ctattccaca | tagcaatgac | atggaatcaa | cccaaatgcc | 1440 |
| catcaatgac | agactggata | aagacaatgt | ggtacatata | caccagggaa | tactgtgcag | 1500 |
| ccacaaaaag | gaacgagatc | atgtcctttg | cagggacatg | gatggagctg | gaagccatta | 1560 |
| tcctcagcaa | actaacacag | gaacagaaaa | ccaagcactg | catgttctca | cttataagtg | 1620 |
| ggagctgaac | aatgaacaca | gggaggggaa | caacacacac | tggggcctgt | tggggagagt | 1680 |
| ggagggaggg | agagcatcag | aaagaatagc | taaaacatga | ggggcttaat | acctaagcaa | 1740 |
| tggattgata | ggtgcagcaa | accaccatgg | cacacattta | cctatgtaac | aactctgcac | 1800 |
| gtcctgtaca | tgtatcccag | aacttaaaac | aaaataaaaa | agataaaaaa | taaataaaac | 1860 |
| acacagtcca | aaaagtcatc | ctgtcttaca | gagctatggg | tgatctggtc | tcctgctact | 1920 |
| ttccgaactt | ctgttctgtt | tccctcaacc | ctctagccta | actacaattg | gcctccttgc | 1980 |
| tgctctggaa | caggccaaga | gcttttctgc | ctcagagtct | ttgcacctgc | catttcctct | 2040 |
| gcttgggaaa | tgtttgcccc | aagggagttg | ggtgacttga | tcgctcacat | tacttaggtc | 2100 |
| tctgcttgaa | tgtcacagat | gttctcttaa | taaagaagag | gcaagaaaag | ccactttatt | 2160 |
| atttattaaa | ctcccgcata | gagtgcagta | ttattactgt | gtgccagacc | ctgcttcaaa | 2220 |
| cacattccat | ggactataaa | attgcatctc | tgagcagctc | ctagagctgg | tagtaacaac | 2280 |

```
ttacatttac tgggtgatta ccatgtgcca ggtattgtgc taaacacgtt gtagatatta   2340
actcacttaa tcctcgtaac aatcccatga agtaggtact gctactatcc cggctttaca   2400
tctgaagtac agagaggtta agtaacttgc cccatgtcat ccagcaagaa ctaaatttga   2460
acccagagct tagccactga tgcctcttga gagaaggagt cagacttaag ttgagtcttt   2520
aaaggtggtt gaccaggcat tgtcagagt taagaaagag aggtaggaca tccttttcca   2580
ggcagagggc attgtgtgca cacacgtata gaagcaggca gcccaccctc atgctttcca   2640
ggaagcaaat gtggctcagg tgtaaagtgc ccggttgatg aagggagtta gcggagggag   2700
tataaggatg tactgtctgc ccccttagga cacctgcaga ggattaaggt ggctgtttct   2760
ccctggaggt ggagtgggtg ggtcactgca caggagccta tagttgttgg tcttttaaac   2820
tcttattggt gtaaccagcc acggaactct gaggcaaggg gttgggggtg ggaagggaaa   2880
cagagaaaag gcaagtgaaa cagaagggga ggtgcagttt cagaacccag ccagcctctc   2940
tcttgctgcc tagcctcctg ccggcctcat cttcgcccag ccaaccccgc ctggagccct   3000
atggccaact gcgagttcag cccggtgtcc gggacaaac cctgctgccg gctctctagg   3060
agagcccaac tctgtcttgg cgtcagtatc ctggtcctga tcctcgtcgt ggtgctcgcg   3120
gtggtcgtcc cgaggtggcg ccagcagtgg agcggtccgg gcaccaccaa gcgctttccc   3180
gagaccgtcc tggcgcgatg cgtcaagtac actgaaattc atcctgagat gaggtgggtt   3240
ggcgactaag gcgcaccggt gggcactgcg gggacagcag ggccccgcgc gcagggaagc   3300
cgcccggatc gcccggaacc gggcatcttc cgtggcgggt cagccgagag cccgccgggt   3360
ggtgctgagt agggagtccc gggctcgggg ctccgcgggc cgctttcagg agcagctggc   3420
cttggcaccg agcgtgcccg cgggaggcgg ggggggcgc tgctcggtgg ctctgctgcg   3480
tagccggtga acacttggca ccgatgcccg ccttctgggc aaggtgccct gagcccagcc   3540
cctcgccggg ctgcagnnnn nnnnnnnnnn nnnnnnnnnn nnnnnnnnnn nnnnnnnnnn   3600
nnnnnnnnnn nnnnnnnnnn nnnnnnnnnn nnnnnnnnnn nnnnnnnnnn nnnnnnatcg   3660
atgttcatca gggatattgg actgaaattt tcttttttta ttgtgtctct gccaggtttc   3720
ggtattagga tgatattggc ctcataaaat gacttatgga ggagtccctc tttttctatt   3780
gtttgcaata gtgtcagaag gaatggtacc agctcctctt tgtaccccctg gtagactgca   3840 tgttagacga gataatatgt atgaactacc tggcatataa tagatgcttc ctaaataaga   3900
ttctaaaaaa taattatgct ccaaaaatat ttttaaaatc aaataattta tgttttattt   3960
tctgtgtttt atctcagaca tgtagactgc caaagtgtat gggatgcttt caagggtgca   4020
tttatttcaa aacatccttg caacattact gaagaagact atcagccact aatgaagttg   4080
ggaactcaga ccgtaccttg caacaaggta attggggggca tgccattgat tttaaaactg   4140
gggataaaag ccaatggtaa caattcatag gtccaaattt ttattagaat gaaggaagag   4200
gaaaaatcca gacattatag tgtgagtgtg gttggtagga atggaatttg caggccattg   4260
aggggccatg atataattaa gatttaggac atctggagaa gggagctaag agagagaaat   4320
agnnnnnnnn nnnnnnnnnn nnnnnnnnnn nnnnnnnnnn nnnnnnnnnn nnnnnnnnnn   4380
nnnnnnnnnn nnnnnnnnnn nnnnnnnnnn nnnnnnnnnn nnttacattg tgacctagaa   4440
cacacacaca cacacacact ctctctccgc cactctcctg cacacagaaa tcattgatgc   4500
ttacaacaat tcttactctt actatgggtg atttactttg atatgctctg ttttttttt   4560 catttacaaa actgtggatt aattttttt gacatgctaa attgatctca gtaatagatt   4620
gtatttattc ttccttagat tcttctttgg agcagaataa aagatctggc ccatcagttc   4680
```

```
acacaggtcc agyggggacat gttcaccctg aggacacgc tgctaggcta ccttgctgat   4740
gacctcacat ggtgtggtga attcaacact tccagtgagg ctctgggccc tgtgggattg   4800
cccagggatg tggaggggtga acagagtgac ttctgctgga ggccctgaat gattagtgtg   4860
gaggacagag ccacaggcac ccatcctgat gccatctata cttatattag tccatttgtg   4920
ttgctattaa ggaatacctg aggctgcgta atttataaag aaaagaggtt tatttgactc   4980
acagttacgc aggctgtaca agaagtaggg taccagcatc cacttcgggt gaaggcctga   5040
ggctgtttcc actcatggag aagggggaagn nnnnnnnnnn nnnnnnnnnn nnnnnnnnnn   5100
nnnnnnnnnn nnnnnnnnnn nnnnnnnnnn nnnnnnnnnn nnnnnnnnnn nnnnnnnnnn   5160
nnnnnnnnng aattcagggg acacttagtt aaattgggtc aaaatgtgtc cattctccag   5220
cctccgtctt ggcagtgaca cattggaaaa tggttccact atgactgaac agccagggaa   5280
gagtacagct tatttatact ctctgttttc cactttattt tctacaaact atgtctttta   5340
gaaataaact atcaatcttg cccagactgg agaaggact gcagcaacaa ccctgtttca   5400
gtattctgga aaacggtttc ccgcagggta agtaccaagt agtgaaattc tagagctttg   5460
gagaccacag aacttaagac gttactcagt cagtgcttgg ttttaacact tttggattac   5520 aaatacttt aggaatgaaa atataggatt cattcctgan nnnnnnnnnn nnnnnnnnnn   5580
nnnnnnnnnn nnnnnnnnnn nnnnnnnnnn nnnnnnnnnn nnnnnnnnnn nnnnnnnnnn   5640
nnnnnnnnnn nnnnnnnnnc tataacactg aacattgttc acttagagat tggagcaact   5700
gcttcaagaa ctctgatatg aagcataatc cgtccagtgg cttggaataa aaattgtgta   5760
gacctgacat tcctgggcta aaaccatatg ggatatcctt ccttaaccag ctattgctaa   5820
gtattgtttt gaatgaaact gctggaggat ggtgattaag tttgcatgat gaatggtggg   5880
catttttttt tttaagtttg cagaagctgc ctgtgatgtg gtccatgtga tgctcaatgg   5940
atcccgcagt aaaatctttg acaaaaacag gtacacattt attttgcatc ctgttttgcaa   6000 gtatcctgtt gcaaatatca cagtgaatat ttcatctcta gaaagaatat gcttttcatg   6060
tttcaggtca gttctgaaga ttaggggccaa aaaaggtaaa aattttgaat tcnnnnnnnn   6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnnnn nnaaagaatc aacattaatg cacaaattaa   6240 gaatttatt ttgagaatct tgttaaccga gggtcatgct gaataagaaa aggttattga   6300
ctgatttgca atttgatgtg tcaactctaa aggataggtc ctagccagtg cctttctgcc   6360
tgctggttgt tgagggggggt gtggatgctt tcgtttgggg ttgatgtttg gggttctttg   6420
tttcttctat tttagcactt tgggagtgt ggaagtccat aatttgcaac cagagaaggt   6480
tcagacacta gaggcctggg tgatacatgg tggaagagaa gattccaggt atatcttact   6540
actttgtacc caagtgttat tttatgaatc agtccacaaa agaatccaca gtcacaagca   6600
cgcactggga acaaattgac tcaggaaatg aaactacatg aatgtgcatg aatcccaaca   6660
gcctcttaac tttatctcca caaaggatat ttaactgctt gacacttcag ctctcctgct   6720
gacccaggag ctcttagagg atttacctct actttacctc tttatccaag ggccttgtcc   6780
agggcgtgct acaaaaacaa agagactcca aaaatgtttg tgagatcttg taattttaat   6840
actttcttct ttcttcccca gagacttatg ccaggatccc accataaaag agctggaatc   6900
gattataagc aaaaggaata ttcaattttc ctgcaagaat atctacaggt aattaatttc   6960
ttcttgaaga aaaaaatgac tgtcttgtca cctgtagaat ttcctttttt ccttagcctc   7020
ctctgagctt ggaggggctgt gtgaatcttt cttgggcctt gatgatgatc acagatggca   7080
```

```
acctctggtg atctctgtcc ctccttccaa nnnnnnnnnn nnnnnnnnnn nnnnnnnnnn    7140
nnnnnnnnnn nnnnnnnnnn nnnnnnnnnn nnnnnnnnnn nnnnnnnnnn nnnnnnnnnn    7200
nnnnnnnnnn aagcttcgga agagaggaaa gcaaattagc cacagaagct gtggggtcc      7260 gtggccttgg ttgctgctcc tgctgttttt ttgaccagca ggtggcatgg atagctcccc    7320
tcccgacatg tcactgcagg agaggagttt atatggatgc taagtggtct gtgcaccttg    7380
tcgtcgctaa aaaggggct tcctccatta gcgaattgga cgacagatgt atcctacggt     7440
ctcttgattt ccttttttgc tttcttgtca tagacctgac aagtttcttc agtgtgtgaa    7500
aaatcctgag gattcatctt gcacatctga gatctgagcc agtcgctgtg gttgttttag    7560
ctccttgact ccttgtggtt tatgtcatca tacatgactc agcatacctg ctggtgcaga    7620
gctgaagatt ttggagggtc ctccacaata aggtcaatgc cagagacgga agcctttttc    7680
cccaaagtct taaataact tatatcatca gcataccttt attgtgatct atcaatagtc     7740 aagaaaatt attgtataag attagaatga aaattgtatg ttaagttact tcactttaat     7800
tctcatgtga tccttttatg ttatttatat attggtaaca tcctttctat tgaaaaatca    7860
ccacaccaaa cctctcttat tagaacaggc aagtgaagaa aagtgaatgc tcaagttttt    7920
cagaaagcat tacatttcca aatgaatgac cttgttgcat gatgtatttt tgtacccttc    7980
ctacagatag tcaaaccata aacttcatgg tcatgggtca tgttggtgaa aattattctg    8040
taggatataa gctacccacg tacttggtgc tttacccccaa cccttccaac agtgctgtga   8100
ggttggtatt atttcatttt ttagatgaga aaatgggagc tcagagaggt tatatattta    8160
agttggtgca aaagtaattg caagttttgc caccgaaagg aatggcaaaa ccacaattat    8220
ttttgagcca acctaataat ttaccgtaag tcctacattt agtatcaagc tagagactga    8280
atttgaactc aactctgtcc aactccaaaa ttcatgtgct ttttccttct aggcctttca    8340
taccaaacta atagtagttt atattctctt ccaacaaatg catattggat taaattgact    8400
agaatggaat ctggaatata gttcttctgg atggctccaa aacacatgtt tttcttcccc    8460
cgtcttcctc ctcctcttca tgctcagtgt tttatatatg tagtatacag ttaaaatata    8520
cttgttgctg gtactggcag cttatatttt ctctcttttt tcatggatta accttgcttg    8580
agggctttaa caattgtatt actttgtcga agaactaagc tt                       8622
```

<210> SEQ ID NO 2
<211> LENGTH: 300
<212> TYPE: PRT
<213> ORGANISM: Homo sapiens
<220> FEATURE:
<221> NAME/KEY: misc_feature
<223> OTHER INFORMATION: human CD38 amino acid sequence (GenBank
      Accession NO.D84284)

<400> SEQUENCE: 2

```
Met Ala Asn Cys Glu Phe Ser Pro Val Ser Gly Asp Lys Pro Cys Cys
1               5                   10                  15

Arg Leu Ser Arg Arg Ala Gln Leu Cys Leu Gly Val Ser Ile Leu Val
            20                  25                  30

Leu Ile Leu Val Val Val Leu Ala Val Val Val Pro Arg Trp Arg Gln
        35                  40                  45

Gln Trp Ser Gly Pro Gly Thr Thr Lys Arg Phe Pro Glu Thr Val Leu
    50                  55                  60

Ala Arg Cys Val Lys Tyr Thr Glu Ile His Pro Glu Met Arg His Val
65                  70                  75                  80
```

| Asp | Cys | Gln | Ser | Val | Trp | Asp | Ala | Phe | Lys | Gly | Ala | Phe | Ile | Ser | Lys |
| | | | | 85 | | | | | 90 | | | | | 95 | |

| His | Pro | Cys | Asn | Ile | Thr | Glu | Glu | Asp | Tyr | Gln | Pro | Leu | Met | Lys | Leu |
| | | | 100 | | | | | 105 | | | | | 110 | | |

| Gly | Thr | Gln | Thr | Val | Pro | Cys | Asn | Lys | Ile | Leu | Leu | Trp | Ser | Arg | Ile |
| | | | 115 | | | | | 120 | | | | | 125 | | |

| Lys | Asp | Leu | Ala | His | Gln | Phe | Thr | Gln | Val | Gln | Arg | Asp | Met | Phe | Thr |
| | 130 | | | | | 135 | | | | | 140 | | | | |

| Leu | Glu | Asp | Thr | Leu | Leu | Gly | Tyr | Leu | Ala | Asp | Asp | Leu | Thr | Trp | Cys |
| 145 | | | | | 150 | | | | | 155 | | | | | 160 |

| Gly | Glu | Phe | Asn | Thr | Ser | Lys | Ile | Asn | Tyr | Gln | Ser | Cys | Pro | Asp | Trp |
| | | | | 165 | | | | | 170 | | | | | 175 | |

| Arg | Lys | Asp | Cys | Ser | Asn | Asn | Pro | Val | Ser | Val | Phe | Trp | Lys | Thr | Val |
| | | | 180 | | | | | 185 | | | | | 190 | | |

| Ser | Arg | Arg | Phe | Ala | Glu | Ala | Ala | Cys | Asp | Val | Val | His | Val | Met | Leu |
| | | | 195 | | | | | 200 | | | | | 205 | | |

| Asn | Gly | Ser | Arg | Ser | Lys | Ile | Phe | Asp | Lys | Asn | Ser | Thr | Phe | Gly | Ser |
| | 210 | | | | | 215 | | | | | 220 | | | | |

| Val | Glu | Val | His | Asn | Leu | Gln | Pro | Glu | Lys | Val | Gln | Thr | Leu | Glu | Ala |
| 225 | | | | | 230 | | | | | 235 | | | | | 240 |

| Trp | Val | Ile | His | Gly | Gly | Arg | Glu | Asp | Ser | Arg | Asp | Leu | Cys | Gln | Asp |
| | | | | 245 | | | | | 250 | | | | | 255 | |

| Pro | Thr | Ile | Lys | Glu | Leu | Glu | Ser | Ile | Ile | Ser | Lys | Arg | Asn | Ile | Gln |
| | | | 260 | | | | | 265 | | | | | 270 | | |

| Phe | Ser | Cys | Lys | Asn | Ile | Tyr | Arg | Pro | Asp | Lys | Phe | Leu | Gln | Cys | Val |
| | | | 275 | | | | | 280 | | | | | 285 | | |

| Lys | Asn | Pro | Glu | Asp | Ser | Ser | Cys | Thr | Ser | Glu | Ile |
| | 290 | | | | | 295 | | | | | 300 |

<210> SEQ ID NO 3
<211> LENGTH: 136
<212> TYPE: DNA
<213> ORGANISM: Homo sapiens
<220> FEATURE:
<221> NAME/KEY: misc_feature
<223> OTHER INFORMATION: human CD38 exon 3 (positions 4639 to 4774 of
      complete cds)
<220> FEATURE:
<221> NAME/KEY: variation
<222> LOCATION: (55)..(55)
<223> OTHER INFORMATION: Description of variation: single nucleotide
      polymorphism involving replacement of (C) and (T)

<400> SEQUENCE: 3
attcttcttt ggagcagaat aaaagatctg gcccatcagt tcacacaggt ccagygggac      60
atgttcaccc tggaggacac gctgctaggc taccttgctg atgacctcac atggtgtggt     120
gaattcaaca cttcca                                                     136

<210> SEQ ID NO 4
<211> LENGTH: 248
<212> TYPE: DNA
<213> ORGANISM: Homo sapiens
<220> FEATURE:
<221> NAME/KEY: misc_feature
<223> OTHER INFORMATION: amplified sequence including human CD38 exon 3
<220> FEATURE:
<221> NAME/KEY: variation
<222> LOCATION: (103)..(103)
<223> OTHER INFORMATION: Description of variation: single nucleotide
      polymorphism involving replacement of (C) and (T)

<400> SEQUENCE: 4

-continued

```
gacatgctaa attgatctca gtaatagatt gtatttattc ttccttagat tcttctttgg    60
agcagaataa aagatctggc ccatcagttc acacaggtcc agyggg acat gttcaccctg   120 gaggacacgc tgctaggcta ccttgctgat gacctcacat ggtgtggtga attcaacact   180
tccagtgagg ctctgggccc tgtgggattg cccagggatg tggagggtga acagagtgac   240
ttctgctg                                                             248

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
ctcctgccgg cctcatcttc                                                 20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
gccctgctgt ccccgcagtg                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
ggcatataat agatgcttcc                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic primer

<400> SEQUENCE: 8
tggacctatg aattgttacc                                                 20

<210> SEQ ID NO 9
<211> LENGTH: 21
<212> TYPE: DNA
<213> ORGANISM: Artificial Sequence
<220> FEATURE:
<223> OTHER INFORMATION: Synthetic primer

<400> SEQUENCE: 9
gacatgctaa attgatctca g                                               21

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
```

```
cagcagaagt cactctgttc                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tccactatga ctgaacagcc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
agcactgact gagtaacgtc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
cttaaccagc tattgctaag                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
actgtgatat ttgcaacagg                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tctgcctgct ggttgttgag                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
tcctgagtca atttgttccc                                               20

<210> SEQ ID NO 17
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 17
ccttgtccag ggcgtgctac                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic primer

<400> SEQUENCE: 18
aagctcagag gaggctaagg                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic primer

<400> SEQUENCE: 19
agcgaattgg acgacagatg                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20 cattgaccttt attgtggagg                                         20
```